(12) United States Patent
Borchert

(10) Patent No.: US 9,926,584 B2
(45) Date of Patent: Mar. 27, 2018

(54) EXPRESSION OF NATIVELY SECRETED POLYPEPTIDES WITHOUT SIGNAL PEPTIDE

(71) Applicant: Novozymes A/S, Bagsvaerd (DK)

(72) Inventor: Martin Simon Borchert, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/898,542

(22) PCT Filed: Jun. 18, 2014

(86) PCT No.: PCT/EP2014/062815
§ 371 (c)(1),
(2) Date: Dec. 15, 2015

(87) PCT Pub. No.: WO2014/206829
PCT Pub. Date: Dec. 31, 2014

(65) Prior Publication Data
US 2016/0130626 A1    May 12, 2016

(30) Foreign Application Priority Data
Jun. 25, 2013  (EP) ..................... 13173651

(51) Int. Cl.
| | | |
|---|---|---|
| *C12N 1/20* | (2006.01) | |
| *C12N 9/00* | (2006.01) | |
| *C12N 9/52* | (2006.01) | |
| *C12N 15/00* | (2006.01) | |
| *C12P 21/06* | (2006.01) | |
| *C12N 15/74* | (2006.01) | |
| *C07H 21/04* | (2006.01) | |
| *C12P 21/02* | (2006.01) | |
| *C12N 15/67* | (2006.01) | |
| *C12N 15/75* | (2006.01) | |
| *C12N 9/24* | (2006.01) | |

(52) U.S. Cl.
CPC .............. *C12P 21/02* (2013.01); *C12N 9/248* (2013.01); *C12N 9/2482* (2013.01); *C12N 9/52* (2013.01); *C12N 15/67* (2013.01); *C12N 15/75* (2013.01); *C12Y 302/01008* (2013.01); *C12Y 304/21062* (2013.01)

(58) Field of Classification Search
None
See application file for complete search history.

(56) References Cited

FOREIGN PATENT DOCUMENTS

| EP | 0994191 A1 | 4/2000 |
| WO | WO-1996-23887 | * 8/1996 |
| WO | 2013/055676 A1 | 4/2013 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36)11643-50.*
Morris et al., Applied and Environmental Microbiology vol. 64, No. 5, pp. 1759-1765 (1998).
Zhang et al., Appl. Biochem. Biotechnol., vol. 160, pp. 1484-1495 (2010).

* cited by examiner

*Primary Examiner* — Iqbal H Chowdhury
(74) *Attorney, Agent, or Firm* — Eric J. Fechter

(57) ABSTRACT

The present invention relates to methods of recombinantly producing a natively secreted polypeptide, the method comprising the steps of providing a microorganism host cell comprising an exogenous polynucleotide encoding a natively secreted polypeptide without a translationally fused signal peptide; cultivating the microorganism host cell under conditions conducive to the expression of the polypeptide and, optionally, recovering the polypeptide, as well as microorganisms, certain polynucleotides, expression constructs and protease substitution variants.

20 Claims, 2 Drawing Sheets

SEQUENCE LISTING

```
<160> NUMBER OF SEQ ID NOS: 19

<210> SEQ ID NO 1
<211> LENGTH: 1965
<212> TYPE: DNA
<213> ORGANISM: Pyrococcus furiosus

<400> SEQUENCE: 1 atgaagggc taaaagctct catattagtg attttagttc taggttttggt agtagggagc      60 gtagcggcag ctccagagaa gaaagttgaa caagtaagaa atgttgagaa gaactatggt     120
ctgctaacgc caggactgtt cagaaaaatt caaaaattga atcctaacga ggaaatcagc     180
acagtaattg tatttgaaaa ccatagggaa aaagaaattg cagtaagagt tcttgagtta     240
atgggtgcaa aagttaggta tgtgtaccat attatacccg caatagctgc cgatcttaag     300
gttagagact tactagtcat ctcaggttta acaggggggta aagctaagct ttcaggtgtt     360
```

```
aggtttatcc aggaagacta caaagttaca gtttcagcag aattagaagg actggatgag    420
tctgcagctc aagttatggc aacttacgtt tggaacttgg gatatgatgg ttctggaatc    480
acaataggaa taattgacac tggaattgac gcttctcatc cagatctcca aggaaaagta    540
attgggtggg tagattttgt caatggtagg agttatccat acgatgacca tggacatgga    600
actcatgtag cttcaatagc agctggtact ggagcagcaa gtaatggcaa gtacaaggga    660
atggctccag gagctaagct ggcgggaatt aaggttctag gtgccgatgg ttctggaagc    720
atatctacta taattaaggg agttgagtgg gccgttgata caaagataa gtacggaatt    780
aaggtcatta atctttctct tggttcaagc cagagctcag atggtactga cgctctaagt    840
caggctgtta atgcagcgtg ggatgctgga ttagttgttg tggttgccgc tggaaacagt    900
ggacctaaca agtatacaat cggttctcca gcagctgcaa gcaaagttat tacagttgga    960
gccgttgaca agtatgatgt tataacaagc ttctcaagca gagggccaac tgcagacggc   1020
aggcttaagc ctgaggttgt tgctccagga aactggataa ttgctgccag agcaagtgga   1080
actagcatgg gtcaaccaat taatgactat tacacagcag ctcctgggac atcaatggca   1140
actcctcacg tagctggtat tgcagccctc ttgctccaag cacacccgag ctggactcca   1200
gacaaagtaa aaacagccct catagaaact gctgatatcg taaagccaga tgaaatagcc   1260
gatatagcct acggtgcagg tagggttaat gcatacaagg ctataaacta cgataactat   1320
gcaaagctag tgttcactgg atatgttgcc aacaaaggca gccaaactca ccagttcgtt   1380
attagcggag cttcgttcgt aactgccaca ttatactggg acaatgccaa tagcgacctt   1440
gatctttacc tctacgatcc caatggaaac caggttgact actcttacac cgcctactat   1500
ggattcgaaa aggttggtta ttacaaccca actgatggaa catggacaat taaggttgta   1560
agctacagcg gaagtgcaaa ctatcaagta gatgtggtaa gtgatggttc cctttcacag   1620
cctggaagtt caccatctcc acaaccagaa ccaacagtag acgcaaagac gttccaagga   1680
tccgttcact actactatga caggagcgac acctttacaa tgaccgttaa ctctggggct   1740
acaaagatta ctggagacct agtgtttgac acaagctacc atgatcttga cctttacctc   1800
tacgatccta accagaagct tgtagataga tcggagagtt ccaacagcta cgaacacgta   1860
gaatacttaa accccgcccc aggaacctgg tacttcctag tatatgccta ctacacttac   1920
ggttgggctt actacgagct gacggctaaa gtttattatg gctga                    1965
```

<210> SEQ ID NO 2
<211> LENGTH: 654
<212> TYPE: PRT
<213> ORGANISM: Pyrococcus furiosus
<220> FEATURE:
<221> NAME/KEY: mat_peptide
<222> LOCATION: (133)..(545)
<223> OTHER INFORMATION: Mature peptide

<400> SEQUENCE: 2

Met Lys Gly Leu Lys Ala Leu Ile Leu Val Ile Leu Val Leu Gly
        -130            -125                -120

Leu Val Val Gly Ser Val Ala Ala Ala Pro Glu Lys Lys Val Glu
        -115            -110                -105

Gln Val Arg Asn Val Glu Lys Asn Tyr Gly Leu Leu Thr Pro Gly Leu
        -100             -95                 -90

Phe Arg Lys Ile Gln Lys Leu Asn Pro Asn Glu Glu Ile Ser Thr Val
         -85             -80                 -75

-continued

```
Ile Val Phe Glu Asn His Arg Glu Lys Glu Ile Ala Val Arg Val Leu
-70             -65                 -60                 -55

Glu Leu Met Gly Ala Lys Val Arg Tyr Val Tyr His Ile Ile Pro Ala
            -50                 -45                 -40

Ile Ala Ala Asp Leu Lys Val Arg Asp Leu Leu Val Ile Ser Gly Leu
                -35                 -30                 -25

Thr Gly Gly Lys Ala Lys Leu Ser Gly Val Arg Phe Ile Gln Glu Asp
            -20                 -15                 -10

Tyr Lys Val Thr Val Ser Ala Glu Leu Glu Gly Leu Asp Glu Ser Ala
    -5                -1   1               5                   10

Ala Gln Val Met Ala Thr Tyr Val Trp Asn Leu Gly Tyr Asp Gly Ser
                15                  20                  25

Gly Ile Thr Ile Gly Ile Ile Asp Thr Gly Ile Asp Ala Ser His Pro
            30                  35                  40

Asp Leu Gln Gly Lys Val Ile Gly Trp Val Asp Phe Val Asn Gly Arg
            45                  50                  55

Ser Tyr Pro Tyr Asp Asp His Gly His Gly Thr His Val Ala Ser Ile
    60                  65                  70

Ala Ala Gly Thr Gly Ala Ala Ser Asn Gly Lys Tyr Lys Gly Met Ala
75              80                  85                  90

Pro Gly Ala Lys Leu Ala Gly Ile Lys Val Leu Gly Ala Asp Gly Ser
            95                  100                 105

Gly Ser Ile Ser Thr Ile Ile Lys Gly Val Glu Trp Ala Val Asp Asn
            110                 115                 120

Lys Asp Lys Tyr Gly Ile Lys Val Ile Asn Leu Ser Leu Gly Ser Ser
            125                 130                 135

Gln Ser Ser Asp Gly Thr Asp Ala Leu Ser Gln Ala Val Asn Ala Ala
            140                 145                 150

Trp Asp Ala Gly Leu Val Val Val Ala Ala Gly Asn Ser Gly Pro
155             160                 165                 170

Asn Lys Tyr Thr Ile Gly Ser Pro Ala Ala Ser Lys Val Ile Thr
                175                 180                 185

Val Gly Ala Val Asp Lys Tyr Asp Val Ile Thr Ser Phe Ser Ser Arg
            190                 195                 200

Gly Pro Thr Ala Asp Gly Arg Leu Lys Pro Glu Val Ala Pro Gly
            205                 210                 215

Asn Trp Ile Ile Ala Ala Arg Ala Ser Gly Thr Ser Met Gly Gln Pro
220                 225                 230

Ile Asn Asp Tyr Tyr Thr Ala Ala Pro Gly Thr Ser Met Ala Thr Pro
235                 240                 245                 250

His Val Ala Gly Ile Ala Ala Leu Leu Leu Gln Ala His Pro Ser Trp
                255                 260                 265

Thr Pro Asp Lys Val Lys Thr Ala Leu Ile Glu Thr Ala Asp Ile Val
            270                 275                 280

Lys Pro Asp Glu Ile Ala Asp Ile Ala Tyr Gly Ala Gly Arg Val Asn
            285                 290                 295

Ala Tyr Lys Ala Ile Asn Tyr Asp Asn Tyr Ala Lys Leu Val Phe Thr
    300                 305                 310

Gly Tyr Val Ala Asn Lys Gly Ser Gln Thr His Gln Phe Val Ile Ser
315                 320                 325                 330

Gly Ala Ser Phe Val Thr Ala Thr Leu Tyr Trp Asp Asn Ala Asn Ser
                335                 340                 345

Asp Leu Asp Leu Tyr Leu Tyr Asp Pro Asn Gly Asn Gln Val Asp Tyr
```

| | | | | 350 | | | | 355 | | | | 360 | |
|---|---|---|---|---|---|---|---|---|---|---|---|---|---|
| Ser | Tyr | Thr | Ala | Tyr | Tyr | Gly | Phe | Glu | Lys | Val | Gly | Tyr | Tyr | Asn | Pro |
| | | | 365 | | | | | 370 | | | | | 375 | |

Thr Asp Gly Thr Trp Thr Ile Lys Val Val Ser Tyr Ser Gly Ser Ala
            380                 385                 390

Asn Tyr Gln Val Asp Val Val Ser Asp Gly Ser Leu Ser Gln Pro Gly
395                 400                 405                 410

Ser Ser Pro Ser Pro Gln Pro Glu Pro Thr Val Asp Ala Lys Thr Phe
                415                 420                 425

Gln Gly Ser Val His Tyr Tyr Tyr Asp Arg Ser Asp Thr Phe Thr Met
            430                 435                 440

Thr Val Asn Ser Gly Ala Thr Lys Ile Thr Gly Asp Leu Val Phe Asp
            445                 450                 455

Thr Ser Tyr His Asp Leu Asp Leu Tyr Leu Tyr Asp Pro Asn Gln Lys
            460                 465                 470

Leu Val Asp Arg Ser Glu Ser Ser Asn Ser Tyr Glu His Val Glu Tyr
475                 480                 485                 490

Leu Asn Pro Ala Pro Gly Thr Trp Tyr Phe Leu Val Tyr Ala Tyr Tyr
                495                 500                 505

Thr Tyr Gly Trp Ala Tyr Tyr Glu Leu Thr Ala Lys Val Tyr Tyr Gly
            510                 515                 520

<210> SEQ ID NO 3
<211> LENGTH: 35
<212> TYPE: DNA
<213> ORGANISM: Artificial sequence
<220> FEATURE:
<223> OTHER INFORMATION: forward primer

<400> SEQUENCE: 3
aaaggagagg ataaagaatg gcacctgaga agaaa                              35

<210> SEQ ID NO 4
<211> LENGTH: 43
<212> TYPE: DNA
<213> ORGANISM: Artificial sequence
<220> FEATURE:
<223> OTHER INFORMATION: reverse primer

<400> SEQUENCE: 4
gcgttttttt attgattaac gcgtttatgg tgatgagcca ggc                     43

<210> SEQ ID NO 5
<211> LENGTH: 1572
<212> TYPE: DNA
<213> ORGANISM: Artificial sequence
<220> FEATURE:
<223> OTHER INFORMATION: Final intended PfuS-encoding DNA fragment.

<400> SEQUENCE: 5
atggcacctg agaagaaagt tgagcaagtt cgcaacgtag agaaaaacta cggtcttctt     60
acaccaggcc ttttccgcaa aatccaaaaa cttaacccta cgaggagat cagcactgta    120 atcgttttg agaaccatcg cgagaaggag atcgctgttc gcgttcttga gcttatgggt    180
gcgaaggtac gctacgttta ccatatcatt ccggctattg cggctgacct taaggttcgc    240
gaccttcttg ttatctctgg tcttactggt ggcaaagcga actttcagg cgttcgcttc    300 atccaagagg actacaaagt tactgtatct gctgagcttg agggacttga cgagtcagcg    360
gcacaagtaa tggcaacata cgtatggaac cttggctacg acggttctgg catcactatc    420

-continued

```
ggcatcatcg acacgggcat cgacgcttca caccctgacc ttcaaggtaa ggtaatcggt    480
tgggttgact tcgttaatgg tcgctcttat ccgtatgacg accatggcca cggtacacac    540
gtagcatcta tcgcagctgg cactggcgca gcttctaacg gcaagtacaa aggcatggca    600
cctggtgcga aacttgctgg tatcaaagta cttggcgcag acggctctgg ctcaatcagc    660
acaatcatca aggcgttga gtgggctgtt gacaacaagg acaaatacgg tatcaaagtt    720
atcaaccttt ctcttggctc ttctcaaagc tctgacggca cagacgcgct ttcacaagct    780
gttaacgctg cttgggacgc tggtcttgta gttgttgttg ctgctggtaa cagcggtcca    840
aacaaataca ctatcggctc accggcagct gcgtctaaag taatcacagt tggagctgta    900
gacaaatacg acgttatcac ttctttctca tctcgtggcc ctactgcaga tggtcgcctt    960
aaaccagagg ttgtagcacc aggcaactgg atcatcgcag ctcgcgcttc tggcacatca   1020
atgggccaac caatcaacga ctactatact gctgcgccag aacttctat ggctactcca   1080 cacgtagcag gtatcgctgc acttcttctt caagctcacc cttcttggac gcctgacaaa   1140
gtaaagactg cacttatcga gactgctgac atcgttaaac ctgacgagat cgcagacatc   1200
gcttatggtg ctggtcgcgt taatgcgtac aaggctatca actatgacaa ctatgctaaa   1260
cttgtattca cgggctacgt agctaacaaa ggctctcaaa cgcaccaatt tgttatctct   1320
ggcgcaagct tcgttactgc tactctttac tgggacaacg ctaactctga ccttgacctt   1380
tacttatacg acccaaacgg caaccaggtt gactattctt atactgcata ctacggcttt   1440
gagaaggttg gctattacaa ccctactgac ggcacatgga caatcaaagt agtaagctat   1500
tcaggatcag ctaactacca gtagacgta gtttctgacg gttctcttag ccagcctggc   1560
tcatcaccat aa                                                       1572
```

<210> SEQ ID NO 6
<211> LENGTH: 523
<212> TYPE: PRT
<213> ORGANISM: Artificial sequence
<220> FEATURE:
<223> OTHER INFORMATION: Intended final PfuS amino acid sequence.
<220> FEATURE:
<221> NAME/KEY: PROPEP
<222> LOCATION: (1)..(110)
<220> FEATURE:
<221> NAME/KEY: mat_peptide
<222> LOCATION: (111)..(523)
<223> OTHER INFORMATION: Mature peptide

<400> SEQUENCE: 6

```
Met  Ala  Pro  Glu  Lys  Lys   Val  Glu  Gln  Val  Arg   Asn  Val  Glu  Lys
-110                 -105                 -100

Asn  Tyr  Gly  Leu  Leu  Thr  Pro  Gly  Leu  Phe  Arg  Lys  Ile  Gln  Lys  Leu
-95                 -90                 -85                  -80

Asn  Pro  Asn  Glu  Glu  Ile  Ser  Thr  Val  Ile  Val  Phe  Glu  Asn  His  Arg
                 -75                 -70                  -65

Glu  Lys  Glu  Ile  Ala  Val  Arg  Val  Leu  Glu  Leu  Met  Gly  Ala  Lys  Val
                 -60                 -55                  -50

Arg  Tyr  Val  Tyr  His  Ile  Ile  Pro  Ala  Ile  Ala  Ala  Asp  Leu  Lys  Val
         -45                 -40                  -35

Arg  Asp  Leu  Leu  Val  Ile  Ser  Gly  Leu  Thr  Gly  Gly  Lys  Ala  Lys  Leu
         -30                 -25                  -20

Ser  Gly  Val  Arg  Phe  Ile  Gln  Glu  Asp  Tyr  Lys  Val  Thr  Val  Ser  Ala
         -15                 -10                  -5                 -1    1
```

```
Glu Leu Glu Gly Leu Asp Glu Ser Ala Ala Gln Val Met Ala Thr Tyr
              5                  10                 15

Val Trp Asn Leu Gly Tyr Asp Gly Ser Gly Ile Thr Ile Gly Ile Ile
             20                  25                 30

Asp Thr Gly Ile Asp Ala Ser His Pro Asp Leu Gln Gly Lys Val Ile
         35                  40                  45

Gly Trp Val Asp Phe Val Asn Gly Arg Ser Tyr Pro Tyr Asp Asp His
50                   55                  60                  65

Gly His Gly Thr His Val Ala Ser Ile Ala Gly Thr Gly Ala Ala
                 70                  75                  80

Ser Asn Gly Lys Tyr Lys Gly Met Ala Pro Gly Ala Lys Leu Ala Gly
             85                  90                  95

Ile Lys Val Leu Gly Ala Asp Gly Ser Gly Ser Ile Ser Thr Ile Ile
            100                 105                 110

Lys Gly Val Glu Trp Ala Val Asp Asn Lys Asp Lys Tyr Gly Ile Lys
            115                 120                 125

Val Ile Asn Leu Ser Leu Gly Ser Ser Gln Ser Ser Asp Gly Thr Asp
130                 135                 140                 145

Ala Leu Ser Gln Ala Val Asn Ala Ala Trp Asp Ala Gly Leu Val Val
                150                 155                 160

Val Val Ala Ala Gly Asn Ser Gly Pro Asn Lys Tyr Thr Ile Gly Ser
                165                 170                 175

Pro Ala Ala Ala Ser Lys Val Ile Thr Val Gly Ala Val Asp Lys Tyr
                180                 185                 190

Asp Val Ile Thr Ser Phe Ser Ser Arg Gly Pro Thr Ala Asp Gly Arg
            195                 200                 205

Leu Lys Pro Glu Val Val Ala Pro Gly Asn Trp Ile Ile Ala Ala Arg
210                 215                 220                 225

Ala Ser Gly Thr Ser Met Gly Gln Pro Ile Asn Asp Tyr Tyr Thr Ala
                230                 235                 240

Ala Pro Gly Thr Ser Met Ala Thr Pro His Val Ala Gly Ile Ala Ala
                245                 250                 255

Leu Leu Leu Gln Ala His Pro Ser Trp Thr Pro Asp Lys Val Lys Thr
            260                 265                 270

Ala Leu Ile Glu Thr Ala Asp Ile Val Lys Pro Asp Glu Ile Ala Asp
275                 280                 285

Ile Ala Tyr Gly Ala Gly Arg Val Asn Ala Tyr Lys Ala Ile Asn Tyr
290                 295                 300                 305

Asp Asn Tyr Ala Lys Leu Val Phe Thr Gly Tyr Val Ala Asn Lys Gly
                310                 315                 320

Ser Gln Thr His Gln Phe Val Ile Ser Gly Ala Ser Phe Val Thr Ala
                325                 330                 335

Thr Leu Tyr Trp Asp Asn Ala Asn Ser Asp Leu Asp Leu Tyr Leu Tyr
            340                 345                 350

Asp Pro Asn Gly Asn Gln Val Asp Ser Tyr Thr Ala Tyr Tyr Gly
            355                 360                 365

Phe Glu Lys Val Gly Tyr Tyr Asn Pro Thr Asp Gly Thr Trp Thr Ile
370                 375                 380                 385

Lys Val Val Ser Tyr Ser Gly Ser Ala Asn Tyr Gln Val Asp Val Val
                390                 395                 400

Ser Asp Gly Ser Leu Ser Gln Pro Gly Ser Ser Pro
            405                 410
```

<210> SEQ ID NO 7
<211> LENGTH: 1572
<212> TYPE: DNA
<213> ORGANISM: Artificial sequence
<220> FEATURE:
<223> OTHER INFORMATION: Actual final PfuS-encoding DNA fragment.

<400> SEQUENCE: 7

```
atggcacctg agaagaaagt tgagcaagtt cgcaacgtag agaaaaacta cggtcttctt      60
acaccaggcc ttttccgcaa atccaaaaa cttaaccca acgaggagat cagcactgta      120
```
*(Note: partial — see below)* atggcacctg agaagaaagt tgagcaagtt cgcaacgtag agaaaaacta cggtcttctt      60
acaccaggcc ttttccgcaa atccaaaaaa cttaacccta acgaggagat cagcactgta     120 atcgttttg agaaccatcg cgagaaggag atcgctgttc gcgttcttga gcttatgggt     180
gcgaaggtac gctacgttta ccatatcatt ccggctattg cggctgacct taaggttcgc     240
gaccttcttg ttatctctgg tcttactggt ggcaaagcga aactttcagg cgttcgcttc     300
atccaagagg actacaaagt tactgtatct gctgagcttg agggacttga cgagtcagcg     360
gcacaagtaa tggcaacata cgtatggaac cttggctacg acggttctgg catcactatc     420
ggcatcatcg acacgggcat cgacgcttca cacctgacc ttcaaggtaa ggtaatcggt     480
tgggttgact tcgttaatgg tcgctcttat ccgtatgacg accatggcca cggtacacac     540
gtagcatcta tcgcagctgg cactggcgca gcttctaacg gcaagtacaa aggcatggca     600
cctggtgcga aacttgctgg tatcaaagta cttggcgcag acggctctgg ctcaatcagc     660
acaatcatca aggcgttga gtgggctgtt gacaacaagg acaaatacgg tatcaaagtt     720
atcaaccttt ctcttggctc ttctcaaagc tctgacggca cagacgcgct ttcacaagct     780
gttaacgctg cttgggacgc tggtcttgta gttgttgttg ctgctggtaa cagcggtcca     840
aacaaataca ctatcggctc accggcagct gcgtctaaag taatcacagt tggagctgta     900
gacaaatacg acgttatcac ttcttctca tctcgtggcc ctactgcaga tggtcgcctt     960
aaaccagagg ttgtagcacc aggcaactgg atcatcgcag ctcgcgcttc tggcacatca    1020
atgggccaac caatcaacga ctactatact gctgcgccag gaacttctat ggctactcca    1080
cacgtagcag gtatcgctgc acttcttctt caagctcacc cttcttggac gcctgacaaa    1140
gtaaagactg cacttatcga gactgctgac atcgttaaac ctgacgagat cgcagacatc    1200
gcttatggtg ctggtcgcgt taatgcgtac aaggctatca actatgacaa ctatgctaaa    1260
cttgtattca cgggctacgt agctaacaaa ggctctcaaa cgcaccaatt tgttatctct    1320
ggcgcaagct tcgttactgc tactcttttac tgggacaacg ctaactctga ccttgacctt    1380
tacttatacg acccaaacgg caaccaggtt gactattctt atactgcata ctacgacttt    1440
gagaaggttg gctattacaa ccctactgac ggcacatgga caatcaaagt agtaagctat    1500
tcaggatcag ctaactacca agtagacgta gtttctgacg gttctcttag ccagcctggc    1560
tcatcaccat aa                                                        1572
```

<210> SEQ ID NO 8
<211> LENGTH: 523
<212> TYPE: PRT
<213> ORGANISM: Artificial sequence
<220> FEATURE:
<223> OTHER INFORMATION: Actual variant PfuS amino acid sequence.
<220> FEATURE:
<221> NAME/KEY: PROPEP
<222> LOCATION: (1)..(110)
<220> FEATURE:
<221> NAME/KEY: mat_peptide
<222> LOCATION: (111)..(523)
<220> FEATURE:
<221> NAME/KEY: VARIANT
<222> LOCATION: (369)..(369)

<223> OTHER INFORMATION: Gly to Asp (G369D) mutation.

<400> SEQUENCE: 8

```
Met Ala Pro Glu Lys Lys Val Glu Gln Val Arg Asn Val Glu Lys
-110            -105                -100

Asn Tyr Gly Leu Leu Thr Pro Gly Leu Phe Arg Lys Ile Gln Lys Leu
-95             -90                 -85                 -80

Asn Pro Asn Glu Glu Ile Ser Thr Val Ile Val Phe Glu Asn His Arg
            -75                 -70                 -65

Glu Lys Glu Ile Ala Val Arg Val Leu Glu Leu Met Gly Ala Lys Val
                -60                 -55                 -50

Arg Tyr Val Tyr His Ile Ile Pro Ala Ile Ala Ala Asp Leu Lys Val
        -45                 -40                 -35

Arg Asp Leu Leu Val Ile Ser Gly Leu Thr Gly Gly Lys Ala Lys Leu
    -30                 -25                 -20

Ser Gly Val Arg Phe Ile Gln Glu Asp Tyr Lys Val Thr Val Ser Ala
-15                 -10                 -5                  -1  1

Glu Leu Glu Gly Leu Asp Glu Ser Ala Ala Gln Val Met Ala Thr Tyr
                5                   10                  15

Val Trp Asn Leu Gly Tyr Asp Gly Ser Gly Ile Thr Ile Gly Ile Ile
            20                  25                  30

Asp Thr Gly Ile Asp Ala Ser His Pro Asp Leu Gln Gly Lys Val Ile
35                  40                  45

Gly Trp Val Asp Phe Val Asn Gly Arg Ser Tyr Pro Tyr Asp Asp His
50                  55                  60                  65

Gly His Gly Thr His Val Ala Ser Ile Ala Ala Gly Thr Gly Ala Ala
            70                  75                  80

Ser Asn Gly Lys Tyr Lys Gly Met Ala Pro Gly Ala Lys Leu Ala Gly
            85                  90                  95

Ile Lys Val Leu Gly Ala Asp Gly Ser Gly Ser Ile Ser Thr Ile Ile
            100                 105                 110

Lys Gly Val Glu Trp Ala Val Asp Asn Lys Asp Lys Tyr Gly Ile Lys
            115                 120                 125

Val Ile Asn Leu Ser Leu Gly Ser Ser Gln Ser Ser Asp Gly Thr Asp
130                 135                 140                 145

Ala Leu Ser Gln Ala Val Asn Ala Ala Trp Asp Ala Gly Leu Val Val
            150                 155                 160

Val Val Ala Ala Gly Asn Ser Gly Pro Asn Lys Tyr Thr Ile Gly Ser
            165                 170                 175

Pro Ala Ala Ala Ser Lys Val Ile Thr Val Gly Ala Val Asp Lys Tyr
            180                 185                 190

Asp Val Ile Thr Ser Phe Ser Ser Arg Gly Pro Thr Ala Asp Gly Arg
            195                 200                 205

Leu Lys Pro Glu Val Val Ala Pro Gly Asn Trp Ile Ile Ala Ala Arg
210                 215                 220                 225

Ala Ser Gly Thr Ser Met Gly Gln Pro Ile Asn Asp Tyr Tyr Thr Ala
            230                 235                 240

Ala Pro Gly Thr Ser Met Ala Thr Pro His Val Ala Gly Ile Ala Ala
            245                 250                 255

Leu Leu Leu Gln Ala His Pro Ser Trp Thr Pro Asp Lys Val Lys Thr
            260                 265                 270

Ala Leu Ile Glu Thr Ala Asp Ile Val Lys Pro Asp Glu Ile Ala Asp
275                 280                 285
```

```
Ile Ala Tyr Gly Ala Gly Arg Val Asn Ala Tyr Lys Ala Ile Asn Tyr
290                 295                 300                 305

Asp Asn Tyr Ala Lys Leu Val Phe Thr Gly Tyr Val Ala Asn Lys Gly
            310                 315                 320

Ser Gln Thr His Gln Phe Val Ile Ser Gly Ala Ser Phe Val Thr Ala
        325                 330                 335

Thr Leu Tyr Trp Asp Asn Ala Asn Ser Asp Leu Asp Leu Tyr Leu Tyr
        340                 345                 350

Asp Pro Asn Gly Asn Gln Val Asp Tyr Ser Tyr Thr Ala Tyr Tyr Asp
        355                 360                 365

Phe Glu Lys Val Gly Tyr Tyr Asn Pro Thr Asp Gly Thr Trp Thr Ile
370                 375                 380                 385

Lys Val Val Ser Tyr Ser Gly Ser Ala Asn Tyr Gln Val Asp Val Val
            390                 395                 400

Ser Asp Gly Ser Leu Ser Gln Pro Gly Ser Ser Pro
            405                 410
```

<210> SEQ ID NO 9
<211> LENGTH: 37
<212> TYPE: DNA
<213> ORGANISM: Artificial sequence
<220> FEATURE:
<223> OTHER INFORMATION: Forward primer

<400> SEQUENCE: 9
tcatcgatcg catcggctgc acctgagaag aaagttg     37

<210> SEQ ID NO 10
<211> LENGTH: 40
<212> TYPE: DNA
<213> ORGANISM: Artificial sequence
<220> FEATURE:
<223> OTHER INFORMATION: Reverse primer

<400> SEQUENCE: 10
ccaaggccgg ttttttatgt tttatggtga tgagccaggc     40

<210> SEQ ID NO 11
<211> LENGTH: 90
<212> TYPE: DNA
<213> ORGANISM: Artificial sequence
<220> FEATURE:
<223> OTHER INFORMATION: DNA encoding the B. clausii aprH protease
      signal peptide.
<220> FEATURE:
<221> NAME/KEY: sig_peptide
<222> LOCATION: (1)..(81)
<223> OTHER INFORMATION: Encodes the signal peptide
<220> FEATURE:
<221> NAME/KEY: misc_feature
<222> LOCATION: (82)..(90)
<223> OTHER INFORMATION: DNA left over from the cloning process.

<400> SEQUENCE: 11
atgaaaaaac cgctggggaa aattgtcgca agcaccgcac tactcatttc tgttgctttt     60
agttcatcga tcgcatcggc tgcacctagg     90

<210> SEQ ID NO 12
<211> LENGTH: 1659
<212> TYPE: DNA
<213> ORGANISM: Artificial sequence
<220> FEATURE:
<223> OTHER INFORMATION: DNA fragment encoding the PfuS protease fused
      N-terminally to the AprH signal peptide.

```
<220> FEATURE:
<221> NAME/KEY: CDS
<222> LOCATION: (1)..(1656)
<223> OTHER INFORMATION: Encodes PfuS protease fused N-terminally to the
      AprH signal peptide.
<220> FEATURE:
<221> NAME/KEY: sig_peptide
<222> LOCATION: (1)..(81)
<223> OTHER INFORMATION: AprH signal peptide
<220> FEATURE:
<221> NAME/KEY: misc_feature
<222> LOCATION: (82)..(417)
<223> OTHER INFORMATION: Propeptide
<220> FEATURE:
<221> NAME/KEY: mat_peptide
<222> LOCATION: (418)..(1656)

<400> SEQUENCE: 12
```

```
atg aaa aaa ccg ctg ggg aaa att gtc gca agc acc gca cta ctc       45
Met Lys Lys Pro Leu Gly Lys Ile Val Ala Ser Thr Ala Leu Leu
             -135             -130             -125 att tct gtt gct ttt agt tca tcg atc gca tcg gct gca cct agg       90
Ile Ser Val Ala Phe Ser Ser Ser Ile Ala Ser Ala Ala Pro Arg
             -120             -115             -110 gca cct gag aag aaa gtt gag caa gtt cgc aac gta gag aaa aac tac  138
Ala Pro Glu Lys Lys Val Glu Gln Val Arg Asn Val Glu Lys Asn Tyr
             -105             -100              -95 ggt ctt ctt aca cca ggc ctt ttc cgc aaa atc caa aaa ctt aac cct  186
Gly Leu Leu Thr Pro Gly Leu Phe Arg Lys Ile Gln Lys Leu Asn Pro
         -90              -85              -80 aac gag gag atc agc act gta atc gtt ttt gag aac cat cgc gag aag  234
Asn Glu Glu Ile Ser Thr Val Ile Val Phe Glu Asn His Arg Glu Lys
         -75              -70              -65 gag atc gct gtt cgc gtt ctt gag ctt atg ggt gcg aag gta cgc tac  282
Glu Ile Ala Val Arg Val Leu Glu Leu Met Gly Ala Lys Val Arg Tyr
         -60              -55              -50 gtt tac cat atc att ccg gct att gcg gct gac ctt aag gtt cgc gac  330
Val Tyr His Ile Ile Pro Ala Ile Ala Ala Asp Leu Lys Val Arg Asp
-45              -40              -35              -30 ctt ctt gtt atc tct ggt ctt act ggt ggc aaa gcg aaa ctt tca ggc  378
Leu Leu Val Ile Ser Gly Leu Thr Gly Gly Lys Ala Lys Leu Ser Gly
         -25              -20              -15 gtt cgc ttc atc caa gag gac tac aaa gtt act gta tct gct gag ctt  426
Val Arg Phe Ile Gln Glu Asp Tyr Lys Val Thr Val Ser Ala Glu Leu
         -10               -5               -1   1 gag gga ctt gac gag tca gcg gca caa gta atg gca aca tac gta tgg  474
Glu Gly Leu Asp Glu Ser Ala Ala Gln Val Met Ala Thr Tyr Val Trp
     5                10               15 aac ctt ggc tac gac ggt tct ggc atc act atc ggc atc atc gac acg  522
Asn Leu Gly Tyr Asp Gly Ser Gly Ile Thr Ile Gly Ile Ile Asp Thr
20               25               30               35 ggc atc gac gct tca cac cct gac ctt caa ggt aag gta atc ggt tgg  570
Gly Ile Asp Ala Ser His Pro Asp Leu Gln Gly Lys Val Ile Gly Trp
             40               45               50 gtt gac ttc gtt aat ggt cgc tct tat ccg tat gac gac cat ggc cac  618
Val Asp Phe Val Asn Gly Arg Ser Tyr Pro Tyr Asp Asp His Gly His
         55               60               65 ggt aca cac gta gca tct atc gca gct ggc act ggc gca gct tct aac  666
Gly Thr His Val Ala Ser Ile Ala Ala Gly Thr Gly Ala Ala Ser Asn
         70               75               80 ggc aag tac aaa ggc atg gca cct ggt gcg aaa ctt gct ggt atc aaa  714
Gly Lys Tyr Lys Gly Met Ala Pro Gly Ala Lys Leu Ala Gly Ile Lys
         85               90               95
```

```
                                                          -continued gta ctt ggc gca gac ggc tct ggc tca atc agc aca atc atc aaa ggc     762
Val Leu Gly Ala Asp Gly Ser Gly Ser Ile Ser Thr Ile Ile Lys Gly
100             105                 110                 115 gtt gag tgg gct gtt gac aac aag gac aaa tac ggt atc aaa gtt atc     810
Val Glu Trp Ala Val Asp Asn Lys Asp Lys Tyr Gly Ile Lys Val Ile
            120                 125                 130 aac ctt tct ctt ggc tct tct caa agc tct gac ggc aca gac gcg ctt     858
Asn Leu Ser Leu Gly Ser Ser Gln Ser Ser Asp Gly Thr Asp Ala Leu
        135                 140                 145 tca caa gct gtt aac gct gct tgg gac gct ggt ctt gta gtt gtt gtt     906
Ser Gln Ala Val Asn Ala Ala Trp Asp Ala Gly Leu Val Val Val Val
    150                 155                 160 gct gct ggt aac agc ggt cca aac aaa tac act atc ggc tca ccg gca     954
Ala Ala Gly Asn Ser Gly Pro Asn Lys Tyr Thr Ile Gly Ser Pro Ala
165                 170                 175 gct gcg tct aaa gta atc aca gtt gga gct gta gac aaa tac gac gtt    1002
Ala Ala Ser Lys Val Ile Thr Val Gly Ala Val Asp Lys Tyr Asp Val
180             185                 190                 195 atc act tct ttc tca tct cgt ggc cct act gca gat ggt cgc ctt aaa    1050
Ile Thr Ser Phe Ser Ser Arg Gly Pro Thr Ala Asp Gly Arg Leu Lys
            200                 205                 210 cca gag gtt gta gca cca ggc aac tgg atc atc gca gct cgc gct tct    1098
Pro Glu Val Val Ala Pro Gly Asn Trp Ile Ile Ala Ala Arg Ala Ser
        215                 220                 225 ggc aca tca atg ggc caa cca atc aac gac tac tat act gct gcg cca    1146
Gly Thr Ser Met Gly Gln Pro Ile Asn Asp Tyr Tyr Thr Ala Ala Pro
    230                 235                 240 gga act tct atg gct act cca cac gta gca ggt atc gct gca ctt ctt    1194
Gly Thr Ser Met Ala Thr Pro His Val Ala Gly Ile Ala Ala Leu Leu
245                 250                 255 ctt caa gct cac cct tct tgg acg cct gac aaa gta aag act gca ctt    1242
Leu Gln Ala His Pro Ser Trp Thr Pro Asp Lys Val Lys Thr Ala Leu
260             265                 270                 275 atc gag act gct gac atc gtt aaa cct gac gag atc gca gac atc gct    1290
Ile Glu Thr Ala Asp Ile Val Lys Pro Asp Glu Ile Ala Asp Ile Ala
            280                 285                 290 tat ggt gct ggt cgc gtt aat gcg tac aag gct atc aac tat gac aac    1338
Tyr Gly Ala Gly Arg Val Asn Ala Tyr Lys Ala Ile Asn Tyr Asp Asn
        295                 300                 305 tat gct aaa ctt gta ttc acg ggc tac gta gct aac aaa ggc tct caa    1386
Tyr Ala Lys Leu Val Phe Thr Gly Tyr Val Ala Asn Lys Gly Ser Gln
    310                 315                 320 acg cac caa ttt gtt atc tct ggc gca agc ttc gtt act gct act ctt    1434
Thr His Gln Phe Val Ile Ser Gly Ala Ser Phe Val Thr Ala Thr Leu
325                 330                 335 tac tgg gac aac gct aac tct gac ctt gac ctt tac tta tac gac cca    1482
Tyr Trp Asp Asn Ala Asn Ser Asp Leu Asp Leu Tyr Leu Tyr Asp Pro
340             345                 350                 355 aac ggc aac cag gtt gac tat tct tat act gca tac tac ggc ttt gag    1530
Asn Gly Asn Gln Val Asp Tyr Ser Tyr Thr Ala Tyr Tyr Gly Phe Glu
            360                 365                 370 aag gtt ggc tat tac aac cct act gac ggc aca tgg aca atc aaa gta    1578
Lys Val Gly Tyr Tyr Asn Pro Thr Asp Gly Thr Trp Thr Ile Lys Val
        375                 380                 385 gta agc tat tca gga tca gct aac tac caa gta gac gta gtt tct gac    1626
Val Ser Tyr Ser Gly Ser Ala Asn Tyr Gln Val Asp Val Val Ser Asp
    390                 395                 400 ggt tct ctt agc cag cct ggc tca tca cca taa                        1659
Gly Ser Leu Ser Gln Pro Gly Ser Ser Pro
405                 410
```

<210> SEQ ID NO 13
<211> LENGTH: 552
<212> TYPE: PRT
<213> ORGANISM: Artificial sequence
<220> FEATURE:
<223> OTHER INFORMATION: Synthetic Construct

<400> SEQUENCE: 13

```
Met Lys Lys Pro Leu Gly Lys Ile Val Ala  Ser Thr Ala Leu Leu
                -135             -130              -125

Ile Ser Val Ala Phe  Ser Ser Ser Ile Ala  Ser Ala Ala Pro Arg
                -120              -115              -110

Ala Pro Glu Lys Lys  Val Glu Gln Val Arg  Asn Val Glu Lys Asn Tyr
                -105              -100               -95

Gly Leu Leu Thr Pro  Gly Leu Phe Arg Lys  Ile Gln Lys Leu Asn Pro
                -90               -85                -80

Asn Glu Glu Ile Ser Thr Val Ile Val Phe Glu Asn His Arg Glu Lys
            -75              -70              -65

Glu Ile Ala Val Arg Val Leu Glu Leu Met Gly Ala Lys Val Arg Tyr
         -60              -55              -50

Val Tyr His Ile Ile Pro Ala Ile Ala Ala Asp Leu Lys Val Arg Asp
-45              -40              -35                  -30

Leu Leu Val Ile Ser Gly Leu Thr Gly Gly Lys Ala Lys Leu Ser Gly
                -25              -20                  -15

Val Arg Phe Ile Gln Glu Asp Tyr Lys Val Thr Val Ser Ala Glu Leu
                -10               -5               -1   1

Glu Gly Leu Asp Glu Ser Ala Ala Gln Val Met Ala Thr Tyr Val Trp
   5                 10                   15

Asn Leu Gly Tyr Asp Gly Ser Gly Ile Thr Ile Gly Ile Ile Asp Thr
20                    25                  30                  35

Gly Ile Asp Ala Ser His Pro Asp Leu Gln Gly Lys Val Ile Gly Trp
                40                  45                  50

Val Asp Phe Val Asn Gly Arg Ser Tyr Pro Tyr Asp Asp His Gly His
                55                  60                  65

Gly Thr His Val Ala Ser Ile Ala Ala Gly Thr Gly Ala Ala Ser Asn
            70                  75                  80

Gly Lys Tyr Lys Gly Met Ala Pro Gly Ala Lys Leu Ala Gly Ile Lys
         85                  90                  95

Val Leu Gly Ala Asp Gly Ser Gly Ser Ile Ser Thr Ile Ile Lys Gly
100                 105                 110                 115

Val Glu Trp Ala Val Asp Asn Lys Asp Lys Tyr Gly Ile Lys Val Ile
                120                 125                 130

Asn Leu Ser Leu Gly Ser Ser Gln Ser Ser Asp Gly Thr Asp Ala Leu
            135                 140                 145

Ser Gln Ala Val Asn Ala Ala Trp Asp Ala Gly Leu Val Val Val Val
            150                 155                 160

Ala Ala Gly Asn Ser Gly Pro Asn Lys Tyr Thr Ile Gly Ser Pro Ala
            165                 170                 175

Ala Ala Ser Lys Val Ile Thr Val Gly Ala Val Asp Lys Tyr Asp Val
180                 185                 190                 195

Ile Thr Ser Phe Ser Ser Arg Gly Pro Thr Ala Asp Gly Arg Leu Lys
                200                 205                 210

Pro Glu Val Val Ala Pro Gly Asn Trp Ile Ile Ala Ala Arg Ala Ser
                215                 220                 225
```

```
Gly Thr Ser Met Gly Gln Pro Ile Asn Asp Tyr Tyr Thr Ala Ala Pro
        230                 235                 240

Gly Thr Ser Met Ala Thr Pro His Val Ala Gly Ile Ala Ala Leu Leu
        245                 250                 255

Leu Gln Ala His Pro Ser Trp Thr Pro Asp Lys Val Lys Thr Ala Leu
260                 265                 270                 275

Ile Glu Thr Ala Asp Ile Val Lys Pro Asp Glu Ile Ala Asp Ile Ala
                280                 285                 290

Tyr Gly Ala Gly Arg Val Asn Ala Tyr Lys Ala Ile Asn Tyr Asp Asn
                295                 300                 305

Tyr Ala Lys Leu Val Phe Thr Gly Tyr Val Ala Asn Lys Gly Ser Gln
            310                 315                 320

Thr His Gln Phe Val Ile Ser Gly Ala Ser Phe Val Thr Ala Thr Leu
        325                 330                 335

Tyr Trp Asp Asn Ala Asn Ser Asp Leu Asp Leu Tyr Leu Tyr Asp Pro
340                 345                 350                 355

Asn Gly Asn Gln Val Asp Tyr Ser Tyr Thr Ala Tyr Tyr Gly Phe Glu
                360                 365                 370

Lys Val Gly Tyr Tyr Asn Pro Thr Asp Gly Thr Trp Thr Ile Lys Val
            375                 380                 385

Val Ser Tyr Ser Gly Ser Ala Asn Tyr Gln Val Asp Val Val Ser Asp
        390                 395                 400

Gly Ser Leu Ser Gln Pro Gly Ser Ser Pro
        405                 410

<210> SEQ ID NO 14
<211> LENGTH: 612
<212> TYPE: DNA
<213> ORGANISM: artificial sequence
<220> FEATURE:
<223> OTHER INFORMATION: A codon-optimized gene encoding the mature
      Dictyoglomus thermophilum xylanase (xylanase-domain only) with an
      N-terminal methionine added.
<220> FEATURE:
<221> NAME/KEY: CDS
<222> LOCATION: (1)..(612)
<223> OTHER INFORMATION: A codon-optimized gene encoding the mature
      Dictyoglomus thermophilum xylanase (xylanase-domain only). An ATG
      translational start codon has been added to the 5'-end of the
      CDS.

<400> SEQUENCE: 14 atg cag aca tca atc aca ctt aca tct aac gca tca ggc aca ttc gac     48
Met Gln Thr Ser Ile Thr Leu Thr Ser Asn Ala Ser Gly Thr Phe Asp
1               5                   10                  15 ggc tat tac tac gag ctt tgg aag gac aca ggc aac acg act atg act     96
Gly Tyr Tyr Tyr Glu Leu Trp Lys Asp Thr Gly Asn Thr Thr Met Thr
            20                  25                  30 gta tac act caa ggt cgc ttc tca tgc cag tgg tct aac atc aac aac    144
Val Tyr Thr Gln Gly Arg Phe Ser Cys Gln Trp Ser Asn Ile Asn Asn
        35                  40                  45 gcg ctt ttc cgc acg ggc aag aag tac aac cag aac tgg caa tct ctt    192
Ala Leu Phe Arg Thr Gly Lys Lys Tyr Asn Gln Asn Trp Gln Ser Leu
    50                  55                  60 ggc act atc cgc atc act tat tct gcg aca tac aac ccg aac ggc aac    240
Gly Thr Ile Arg Ile Thr Tyr Ser Ala Thr Tyr Asn Pro Asn Gly Asn
65                  70                  75                  80 tct tac ctt tgt atc tac ggc tgg tct acg aac ccg ctt gtt gag ttc    288
Ser Tyr Leu Cys Ile Tyr Gly Trp Ser Thr Asn Pro Leu Val Glu Phe
                85                  90                  95
```

```
tac atc gta gag tct tgg ggc aac tgg cgt cct cct ggc gca aca tct       336
Tyr Ile Val Glu Ser Trp Gly Asn Trp Arg Pro Pro Gly Ala Thr Ser
            100                 105                 110 ctt ggc cag gtt aca atc gat ggt ggc aca tat gac atc tac cgc act       384
Leu Gly Gln Val Thr Ile Asp Gly Gly Thr Tyr Asp Ile Tyr Arg Thr
        115                 120                 125 act cgc gtt aac cag cct agc atc gtt ggc aca gct act ttc gac caa       432
Thr Arg Val Asn Gln Pro Ser Ile Val Gly Thr Ala Thr Phe Asp Gln
130                 135                 140 tac tgg agc gtt cgc act agc aag cgc aca tct ggc aca gtt acg gtt       480
Tyr Trp Ser Val Arg Thr Ser Lys Arg Thr Ser Gly Thr Val Thr Val
145                 150                 155                 160 acg gac cac ttt cgc gca tgg gca aat cgt ggc ctt aac ctt ggc aca       528
Thr Asp His Phe Arg Ala Trp Ala Asn Arg Gly Leu Asn Leu Gly Thr
                165                 170                 175 atc gac caa atc aca ctt tgt gtt gag ggc tac cag tct tct ggc agc       576
Ile Asp Gln Ile Thr Leu Cys Val Glu Gly Tyr Gln Ser Ser Gly Ser
            180                 185                 190 gca aac atc act caa aac act ttc tct cag ggc agc                       612
Ala Asn Ile Thr Gln Asn Thr Phe Ser Gln Gly Ser
        195                 200

<210> SEQ ID NO 15
<211> LENGTH: 204
<212> TYPE: PRT
<213> ORGANISM: artificial sequence
<220> FEATURE:
<223> OTHER INFORMATION: Synthetic Construct

<400> SEQUENCE: 15

Met Gln Thr Ser Ile Thr Leu Thr Ser Asn Ala Ser Gly Thr Phe Asp
1               5                   10                  15

Gly Tyr Tyr Tyr Glu Leu Trp Lys Asp Thr Gly Asn Thr Thr Met Thr
            20                  25                  30

Val Tyr Thr Gln Gly Arg Phe Ser Cys Gln Trp Ser Asn Ile Asn Asn
        35                  40                  45

Ala Leu Phe Arg Thr Gly Lys Lys Tyr Asn Gln Asn Trp Gln Ser Leu
    50                  55                  60

Gly Thr Ile Arg Ile Thr Tyr Ser Ala Thr Tyr Asn Pro Asn Gly Asn
65                  70                  75                  80

Ser Tyr Leu Cys Ile Tyr Gly Trp Ser Thr Asn Pro Leu Val Glu Phe
                85                  90                  95

Tyr Ile Val Glu Ser Trp Gly Asn Trp Arg Pro Pro Gly Ala Thr Ser
            100                 105                 110

Leu Gly Gln Val Thr Ile Asp Gly Gly Thr Tyr Asp Ile Tyr Arg Thr
        115                 120                 125

Thr Arg Val Asn Gln Pro Ser Ile Val Gly Thr Ala Thr Phe Asp Gln
130                 135                 140

Tyr Trp Ser Val Arg Thr Ser Lys Arg Thr Ser Gly Thr Val Thr Val
145                 150                 155                 160

Thr Asp His Phe Arg Ala Trp Ala Asn Arg Gly Leu Asn Leu Gly Thr
                165                 170                 175

Ile Asp Gln Ile Thr Leu Cys Val Glu Gly Tyr Gln Ser Ser Gly Ser
            180                 185                 190

Ala Asn Ile Thr Gln Asn Thr Phe Ser Gln Gly Ser
        195                 200
```

<210> SEQ ID NO 16
<211> LENGTH: 8623
<212> TYPE: DNA
<213> ORGANISM: artificial sequence
<220> FEATURE:
<223> OTHER INFORMATION: Plasmid pJA4156 (see Figure 1; example 4).

<400> SEQUENCE: 16

| | | | | | |
|---|---|---|---|---|---|
| ggtaccagat | ctaatatctt | tgaattgtaa | cgcccctcaa | agtaagaac | tacaaaaaaa | 60 |
| gaatacgtta | tatagaaata | tgtttgaacc | ttcttcagat | tacaaatata | ttcggacgga | 120 |
| ctctacctca | aatgcttatc | taactataga | atgacataca | agcacaacct | tgaaaatttg | 180 |
| aaaatataac | taccaatgaa | cttgttcatg | tgaattatcg | ctgtatttaa | ttttctcaat | 240 |
| tcaatatata | atatgccaat | acattgttac | aagtagaaat | taagacaccc | ttgatagcct | 300 |
| tactataccc | aacatgatgt | agtattaaat | gaatatgtaa | atatatttat | gataagaagc | 360 |
| gacttattta | taatcattac | atatttttct | attggaatga | ttaagattcc | aatagaatag | 420 |
| tgtataaatt | atttatcttg | aaaggaggga | tgcctaaaaa | cgaagaacat | taaaaacata | 480 |
| tatttgcacc | gtctaatgga | tagaaaggag | gtgatccagc | cgcaccttat | gaaaaatcat | 540 |
| tttatcagtt | tgaaaattat | gtattatgga | gctctataaa | aatgaggagg | gaaccgaatg | 600 |
| cagacatcaa | tcacacttac | atctaacgca | tcaggcacat | tcgacggcta | ttactacgag | 660 |
| ctttggaagg | acacaggcaa | cacgactatg | actgtataca | ctcaaggtcg | cttctcatgc | 720 |
| cagtggtcta | acatcaacaa | cgcgctttc | cgcacgggca | agaagtacaa | ccagaactgg | 780 |
| caatctcttg | gcactatccg | catcacttat | tctgcgacat | acaacccgaa | cggcaactct | 840 |
| tacctttgta | tctacggctg | gtctacgaac | ccgcttgttg | agttctacat | cgtagagtct | 900 |
| tggggcaact | ggcgtcctcc | tggcgcaaca | ctctcttggcc | aggttacaat | cgatggtggc | 960 |
| acatatgaca | tctaccgcac | tactcgcgtt | aaccagccta | gcatcgttgg | cacagctact | 1020 |
| ttcgaccaat | actggagcgt | tcgcactagc | aagcgcacat | ctggcacagt | tacggttacg | 1080 |
| gaccactttc | gcgcatgggc | aaatcgtggc | cttaaccttg | gcacaatcga | ccaaatcaca | 1140 |
| ctttgtgttg | agggctacca | gtcttctggc | agcgcaaaca | tcactcaaaa | cactttctct | 1200 |
| cagggcagct | aacgcgtagg | gcccgcggct | agcggccgcg | tcgactagaa | gagcagagag | 1260 |
| gacggatttc | ctgaaggaaa | tccgtttttt | tattttgccc | gtcttataaa | tttcgttgtc | 1320 |
| caactcgctt | aattgcgagt | ttttatttcg | tttatttcaa | ttaaggtaac | taaagatcct | 1380 |
| ctagagtcga | ttatgtcttt | tgcgcagtcg | gcttaaacca | gttttcgctg | gtgcgaaaaa | 1440 |
| agagtgtctt | gtgacaccta | aattcaaaat | ctatcggtca | gatttatacc | gatttgattt | 1500 |
| tatatattct | tgaataacat | acgccgagtt | atcacataaa | agcgggaacc | aatcatcaaa | 1560 |
| tttaaacttc | attgcataat | ccattaaact | cttaaattct | acgattcctt | gttcatcaat | 1620 |
| aaactcaatc | atttctttaa | ttaatttata | tctatctgtt | gttgttttct | ttaataattc | 1680 |
| atcaacatct | acaccgccat | aaactatcat | atcttctttt | tgatatttaa | atttattagg | 1740 |
| atcgtccatg | tgaagcatat | atctcacaag | acctttcaca | cttcctgcaa | tctgcggaat | 1800 |
| agtcgcattc | aattcttctg | taattatttt | tatctgttca | taagatttat | taccctcata | 1860 |
| catcactaga | atatgataat | gctcttttt | catcctacct | tctgtatcag | tatccctatc | 1920 |
| atgtaatgga | gacactacaa | attgaatgtg | taactctttt | aaatactcta | accactcggc | 1980 |
| ttttgctgat | tctggatata | aaacaaatgt | ccaattacgt | cctcttgaat | ttttcttgtt | 2040 |
| ttcagtttct | tttattacat | tttcgctcat | gatataataa | cggtgctaat | acacttaaca | 2100 |

```
aaatttagtc atagataggc agcatgccag tgctgtctat cttttttgt ttaaaatgca   2160
ccgtattcct cctttgcata ttttttatt agaataccgg ttgcatctga tttgctaata   2220
ttatatttt ctttgattct atttaatatc tcattttctt ctgttgtaag tcttaaagta   2280
acagcaactt ttttctcttc ttttctatct acaaccatca ctgtacctcc caacatctgt   2340
tttttcact ttaacataaa aacaacctt ttaacattaa aaacccaata tttatttatt    2400
tgtttggaca atggacaatg gacacctagg ggggaggtcg tagtacccccc ctatgttttc  2460
tcccctaaat aaccccaaaa atctaagaaa aaagacctc aaaaaggtct ttaattaaca   2520
tctcaaattt cgcatttatt ccaatttcct ttttgcgtgt gatgcgctgc gtccattaaa   2580
aatcctagag ctttgaaacc gaaagttaat agctgtcgct actactttcg cttacgctct   2640
aagtatattt taaggactgt cacacgcaaa aagttttctc ggcataaaag tacctctaca   2700
tctctaaatc gtctgtacgc tgtttctcac gctttctatc gaccttctgg acattatcct   2760
gtacaacatc cataaactgt cccacacgct caaatttgga atcattaaag aatttctctt   2820
taagcctatt aaacccttc tcaaacccag ggaaattcgc cctcgcagca cgatataaag   2880
tcactgtact agcttgaaat ttctctgata cattcaactg ctcattcaaa ctatcattct   2940
ctcgctttaa tttattaacc tctttacttt tttcgtgata ccctctttc catgtattca   3000
ctacttcttt caaactctct ctacgttttt taattcttg attttctgtg taatagtctg   3060
tgctcttaat attttcgtaa tcatcaacaa tccgttctgc agaagagatt gtttcttgca   3120
ggcgttcaaa ttcatcagca gttaatatct ttctaccagt ctcttcacgt ccagagaaca   3180
aacctgtacg ctcatttca taatcaaagg gtttcgtaga cctcatatgc tctattccac   3240
tctgtaactg cttatttgcc ttctgtaact catccttaac ttcttgcagt tcctgtttat   3300
gaaatacagt atctttcttg tactgatcca tcgctttatg ttctcgttct gtaacctctt   3360
tggacgtgcc tctttcaagt tcataacctt tctcattcac atactcatta aatctatctt   3420
gtaattgagt aaagtctttc ttgttgccta actgttcttt tgcagacaat ctcccgtcct   3480
ctgttaaagg gacaaaacca aagtgcatat gtgggactct ttcatccaga tggacagtcg   3540
catacagcat attttcctta ccgtattcat tttctagaaa ctccaagcta tcttaaaaa   3600
atcgttctat ttcttctccg cttaaatcat caaagaaatc tttatcactt gtaaccagtc   3660
cgtccacatg tcgaattgca tctgaccgaa ttttacgttt ccctgaataa ttctcatcaa   3720
tcgtttcatc aattttatct ttatacttta tattttgtgc gttaatcaaa tcataatttt   3780
tatatgtttc ctcatgattt atgtctttat tattatagtt tttattctct ctttgattat   3840
gtctttgtat cccgtttgta ttacttgatc ctttaactct ggcaaccctc aaaattgaat   3900
gagacatgct acacctccgg ataataaata tatataaacg tatatagatt tcataaagtc   3960
taacacacta gacttattta cttcgtaatt aagtcgttaa accgtgtgct ctacgaccaa   4020
aactataaaa cctttaagaa cttttcttttt ttacaagaaa aagaaatta gataaatctc   4080
tcatatcttt tattcaataa tcgcatccga ttgcagtata aatttaacga tcactcatca   4140
tgttcatatt tatcagagct cgtgctataa ttatactaat tttataagga ggaaaaaata   4200
tgggcatttt tagtattttt gtaatcagca cagttcatta tcaaccaaac aaaaaataag   4260
tggttataat gaatcgttaa taagcaaaat tcatataacc aaattaaaga gggttataat   4320
gaacgagaaa aatataaaac acagtcaaaa ctttattact tcaaaacata atatagataa   4380
aataatgaca aatataagat taaatgaaca tgataatatc tttgaaatcg gctcaggaaa   4440
aggccatttt acccttgaat tagtaaagag gtgtaatttc gtaactgcca ttgaaataga   4500
```

```
ccataaatta tgcaaaacta cagaaaataa acttgttgat cacgataatt tccaagtttt   4560
aaacaaggat atattgcagt ttaaatttcc taaaaaccaa tcctataaaa tatatggtaa   4620
tataccttat aacataagta cggatataat acgcaaaatt gttttgata gtatagctaa    4680 tgagatttat ttaatcgtgg aatacgggtt tgctaaaaga ttattaaata caaacgctc    4740 attggcatta cttttaatgg cagaagttga tatttctata ttaagtatgg ttccaagaga   4800
atattttcat cctaaaccta aagtgaatag ctcacttatc agattaagta gaaaaaaatc   4860
aagaatatca cacaaagata aacaaaagta taattatttc gttatgaaat gggttaacaa   4920
agaatacaag aaaatatttta caaaaatca atttaacaat tccttaaaac atgcaggaat   4980
tgacgattta aacaatatta gctttgaaca attcttatct cttttcaata gctataaatt   5040
atttaataag taagttaagg gatgcataaa ctgcatccct taacttgttt ttcgtgtgcc   5100
tattttttgt gaatcgacct gcaggcatgc aagcttaagc gagttggaat ttaaatatga   5160
tatctacatt atcagcagta acatcaacct ttgatacaag gttgttgacg attttctttt   5220
tattatcata tgatagttca ttaatcggaa ttgagcccaa ctgagtttta actaactcaa   5280
aaacatcagt agagtcatta aatttatttt cgctaatctt agctttaagc agcttttttct  5340 cagcctgaag ggaatcagta cgatctttca actcatccat agtgataaaa tcatttaggt   5400
acaaatcaga gttcttttgt atttttttat cgatctgtga aatttgcttt ttaaatgacg   5460
aagtatcaag aataggttgg ttgttgccat tgataatttt caataaggag tcattatttt   5520
cttgaaatcc aatcaggttg tcaataacag tattttctaa attacttaaa tcataagttc   5580
ctgaatcaca cttttattg tcattatata ctgtaattcc ttttgttttt cgaggaaatc    5640
tatttgcaca gtgatatttc atagtgcggc ttccatcttt tcttttgtgg ccaagaacaa   5700
tttttaaagg tgctccacag taaccgcacc ttgccatccc tgacagcata tatttagctt   5760
ggaaaggtct agggttgtta tttctttcat aagtctgctg ttgtcttctct tctagctctt   5820 tttgaacttt taaataagtc tcataaggga taattggttt gtgcatacct tcaaataggc   5880
tgtccttaaa tttgatataa ccacagtaaa ctggattatc aagtgtttgt cttagggtac   5940
gataagacca cggtatatct ttaccgatgt gtccagattc attgagttta tctcttaatt   6000
ttgtaagtga tattcctgat aaataatcag tgaatatttg ttcaactatt gtagcttgta   6060
aaggaacaat ttctaatata cctgtctttc tgttgtggta atacccaaaa gctgtcttag   6120
tccacatcat agacttacca gatttcgctc gccctagttt acccatagtc atgcgttctt   6180
ttatattctc tcttttcaaac tcattaattg cagaaagaat agtgagaaac aagctaccca   6240
tagcagaaga agtatcaata ctttcattaa gcgagataaa gtctatttta ttttttgtga   6300
acacatcctt aacaagataa agagtatctc ttacactacg tgaaaggcgg tctagcttat   6360
atacaagaac tgtatcaaaa gcttattct cgatatcgtt gattaatctt tgcattgctg    6420
ggcgttcaag tttggcccct gaaaaaccag catcagtata agtatcagat acttgccacc   6480
ccattgcttc agcatatttt gttaaacggt caatttgctc atcaattgag aaccttcct    6540 ctgcttggtt agtagtggat actcgtgtat agattgctac tttcttagtc atgagatttc   6600 cccccttaaaa ataaattcat tcaaatacag atgcatttta tttcatatag taagtacatc   6660
acctattagt tgttgtttta aacaaactaa cttattttca tcttatatag cctcgtcagt   6720
attttcaata tttttttag tttttttatga acacattaga tataataaag ggaagattcg   6780
ctatgtacta tgttgatact taatttaaag attaaacaaa tggagtggat gaagtggata   6840
```

```
tcgctgatca aacctttgtc aaaaaagtaa atcaaaagtt attattaaaa gaaatcctta      6900
aaaattcacc tatttcaaga gcaaaattat ctgaaatgac tggattaaat aaatcaactg      6960
tctcatcaca ggtaaacacg ttaatgaaag aaagtatggt atttgaaata ggtcaaggac      7020
aatcaagtgg cggaagaaga cctgtcatgc ttgtttttaa taaaaaggca ggatactccg      7080
ttggaataga tgttggtgtg gattatatta atggcatttt aacagacctt gaaggaacaa      7140
tcgttcttga tcaataccgc catttggaat ccaattctcc agaaataacg aaagacattt      7200
tgattgatat gattcatcac tttattacgc aaatgcccca atctccgtac gggcttattg      7260
gtataggtat ttgcgtgcct ggactcattg ataaagatca aaaaattgtt ttcactccga      7320
actccaactg gagagatatt gacttaaaat cttcgataca agagaagtac aatgtgcctg      7380 ttttattga aaatgaggca aatgctggcg catatggaga aaaagtattt ggagctgcaa       7440
aaaatcacga taacattatt tacgtaagta tcagcacagg aatagggatc ggtgttatta      7500
tcaacaatca tttatataga ggagtaagcg gcttctctgg agaaatggga catatgacaa      7560
tagactttaa tggtcctaaa tgcagttgcg gaaaccgagt atgctgggaa ttgtatgctt      7620
cagagaaggc tttattaaaa tctcttcaga ccaaagagaa aaaactgtcc tatcaagata      7680
tcataaacct cgcccatctg aatgatatcg gaaccttaaa tgcattacaa aattttggat      7740
tctatttagg aataggcctt accaatattc taaatacttt caacccacaa gccgtaattt      7800
taagaaatag cataattgaa tcgcatccta tggttttaaa ttcaatgaga agtgaagtat      7860
catcaagggt ttattcccaa ttaggcaata gctatgaatt attgccatct tccttaggac      7920
agaatgcacc ggcattagga atgtcctcca ttgtgattga tcattttctg gacatgatta      7980
caatgtaatt ttttatggaa tggacagctc atctttaaag atgagttttt ttattctagg      8040
agtatttctg aattcgagct cgttattaat ctgttcagca atcgggcgcg attgctgaat      8100
aaaagatacg agagacctct cttgtatctt ttttattttg agtggttttg tccgttacac      8160
tagaaaaccg aaagacaata aaaatttat tcttgctgag tctggctttc ggtaagctag        8220
acaaaacgga caaaataaaa attggcaagg gtttaaaggt ggagattttt tgagtgatct      8280
tctcaaaaaa tactacctgt cccttgctga tttttaaacg agcacgagag caaaaccccc      8340 cttttgctgag gtggcagagg gcaggttttt ttgtttcttt tttctcgtaa aaaaaagaaa    8400
ggtcttaaag gttttatggt tttggtcggc actgccgaca gcctcgcaga gcacacactt      8460
tatgaatata aagtatagtg tgttatactt tacttggaag tggttgccgg aaagagcgaa     8520
aatgcctcac atttgtgcca cctaaaaagg agcgatttac atatgagtta tgcagtttgt     8580
agaatgcaaa aagtgaaatc agctggacta aaaggcagag ctc                         8623
```

<210> SEQ ID NO 17
<211> LENGTH: 696
<212> TYPE: DNA
<213> ORGANISM: artificial sequence
<220> FEATURE:
<223> OTHER INFORMATION: Codon-optimized gene encoding the mature
      Dictyoglomus thermophilum xylanase (xylanase-domain only) with an
      artificial secretion signal added to the 5'-end of the CDS.
<220> FEATURE:
<221> NAME/KEY: CDS
<222> LOCATION: (1)..(696)
<223> OTHER INFORMATION: The codon-optimized gene of SEQ ID NO:14
      encoding the mature Dictyoglomus thermophilum xylanase (xylanase-
      domain only) with an artificial secretion signal (insted of the
      ATG translational start codon) added to the 5'-end of the CDS.
<220> FEATURE:
<221> NAME/KEY: sig_peptide
<222> LOCATION: (1)..(87)

<223> OTHER INFORMATION: Secretion signal peptide.
<220> FEATURE:
<221> NAME/KEY: mat_peptide
<222> LOCATION: (88)..(696)
<223> OTHER INFORMATION: Mature Dictyoglomus thermophilum xylanase (xylanase-domain only).

<400> SEQUENCE: 17

| | | | | | | | | | | | | | | | | |
|---|---|---|---|---|---|---|---|---|---|---|---|---|---|---|---|---|
| atg | aaa | caa | caa | aaa | cgg | ctt | tac | gcc | cga | ttg | gtg | ctt | atg | tgc | acg | 48 |
| Met | Lys | Gln | Gln | Lys | Arg | Leu | Tyr | Ala | Arg | Leu | Val | Leu | Met | Cys | Thr | |
| | | | -25 | | | | -20 | | | | | -15 | | | | |
| ctg | tta | ttt | gtc | agt | ttg | ccg | att | aca | aaa | aca | tca | gcc | cag | aca | tca | 96 |
| Leu | Leu | Phe | Val | Ser | Leu | Pro | Ile | Thr | Lys | Thr | Ser | Ala | Gln | Thr | Ser | |
| | | | -10 | | | | -5 | | | | -1 | 1 | | | | |
| atc | aca | ctt | aca | tct | aac | gca | tca | ggc | aca | ttc | gac | ggc | tat | tac | tac | 144 |
| Ile | Thr | Leu | Thr | Ser | Asn | Ala | Ser | Gly | Thr | Phe | Asp | Gly | Tyr | Tyr | Tyr | |
| | | | 5 | | | | 10 | | | | 15 | | | | | |
| gag | ctt | tgg | aag | gac | aca | ggc | aac | acg | act | atg | act | gta | tac | act | caa | 192 |
| Glu | Leu | Trp | Lys | Asp | Thr | Gly | Asn | Thr | Thr | Met | Thr | Val | Tyr | Thr | Gln | |
| 20 | | | | | 25 | | | | | 30 | | | | | 35 | |
| ggt | cgc | ttc | tca | tgc | cag | tgg | tct | aac | atc | aac | aac | gcg | ctt | ttc | cgc | 240 |
| Gly | Arg | Phe | Ser | Cys | Gln | Trp | Ser | Asn | Ile | Asn | Asn | Ala | Leu | Phe | Arg | |
| | | | | 40 | | | | | 45 | | | | | 50 | | |
| acg | ggc | aag | aag | tac | aac | cag | aac | tgg | caa | tct | ctt | ggc | act | atc | cgc | 288 |
| Thr | Gly | Lys | Lys | Tyr | Asn | Gln | Asn | Trp | Gln | Ser | Leu | Gly | Thr | Ile | Arg | |
| | | | 55 | | | | | 60 | | | | | 65 | | | |
| atc | act | tat | tct | gcg | aca | tac | aac | ccg | aac | ggc | aac | tct | tac | ctt | tgt | 336 |
| Ile | Thr | Tyr | Ser | Ala | Thr | Tyr | Asn | Pro | Asn | Gly | Asn | Ser | Tyr | Leu | Cys | |
| | | | | 70 | | | | | 75 | | | | | 80 | | |
| atc | tac | ggc | tgg | tct | acg | aac | ccg | ctt | gtt | gag | ttc | tac | atc | gta | gag | 384 |
| Ile | Tyr | Gly | Trp | Ser | Thr | Asn | Pro | Leu | Val | Glu | Phe | Tyr | Ile | Val | Glu | |
| | 85 | | | | | 90 | | | | | 95 | | | | | |
| tct | tgg | ggc | aac | tgg | cgt | cct | cct | ggc | gca | aca | tct | ctt | ggc | cag | gtt | 432 |
| Ser | Trp | Gly | Asn | Trp | Arg | Pro | Pro | Gly | Ala | Thr | Ser | Leu | Gly | Gln | Val | |
| 100 | | | | | 105 | | | | | 110 | | | | | 115 | |
| aca | atc | gat | ggt | ggc | aca | tat | gac | atc | tac | cgc | act | act | cgc | gtt | aac | 480 |
| Thr | Ile | Asp | Gly | Gly | Thr | Tyr | Asp | Ile | Tyr | Arg | Thr | Thr | Arg | Val | Asn | |
| | | | | 120 | | | | | 125 | | | | | 130 | | |
| cag | cct | agc | atc | gtt | ggc | aca | gct | act | ttc | gac | caa | tac | tgg | agc | gtt | 528 |
| Gln | Pro | Ser | Ile | Val | Gly | Thr | Ala | Thr | Phe | Asp | Gln | Tyr | Trp | Ser | Val | |
| | | | 135 | | | | | 140 | | | | | 145 | | | |
| cgc | act | agc | aag | cgc | aca | tct | ggc | aca | gtt | acg | gtt | acg | gac | cac | ttt | 576 |
| Arg | Thr | Ser | Lys | Arg | Thr | Ser | Gly | Thr | Val | Thr | Val | Thr | Asp | His | Phe | |
| | | | | 150 | | | | | 155 | | | | | 160 | | |
| cgc | gca | tgg | gca | aat | cgt | ggc | ctt | aac | ctt | ggc | aca | atc | gac | caa | atc | 624 |
| Arg | Ala | Trp | Ala | Asn | Arg | Gly | Leu | Asn | Leu | Gly | Thr | Ile | Asp | Gln | Ile | |
| | | | 165 | | | | | 170 | | | | | 175 | | | |
| aca | ctt | tgt | gtt | gag | ggc | tac | cag | tct | tct | ggc | agc | gca | aac | atc | act | 672 |
| Thr | Leu | Cys | Val | Glu | Gly | Tyr | Gln | Ser | Ser | Gly | Ser | Ala | Asn | Ile | Thr | |
| 180 | | | | | 185 | | | | | 190 | | | | | 195 | |
| caa | aac | act | ttc | tct | cag | ggc | agc | | | | | | | | | 696 |
| Gln | Asn | Thr | Phe | Ser | Gln | Gly | Ser | | | | | | | | | |
| | | | | 200 | | | | | | | | | | | | |

<210> SEQ ID NO 18
<211> LENGTH: 232
<212> TYPE: PRT
<213> ORGANISM: artificial sequence
<220> FEATURE:
<223> OTHER INFORMATION: Synthetic Construct

<400> SEQUENCE: 18

```
Met Lys Gln Gln Lys Arg Leu Tyr Ala Arg Leu Val Leu Met Cys Thr
            -25                 -20                 -15

Leu Leu Phe Val Ser Leu Pro Ile Thr Lys Thr Ser Ala Gln Thr Ser
            -10                  -5                  -1   1

Ile Thr Leu Thr Ser Asn Ala Ser Gly Thr Phe Asp Gly Tyr Tyr Tyr
  5                  10                  15

Glu Leu Trp Lys Asp Thr Gly Asn Thr Thr Met Thr Val Tyr Thr Gln
 20                  25                  30                  35

Gly Arg Phe Ser Cys Gln Trp Ser Asn Ile Asn Asn Ala Leu Phe Arg
                 40                  45                  50

Thr Gly Lys Lys Tyr Asn Gln Asn Trp Gln Ser Leu Gly Thr Ile Arg
             55                  60                  65

Ile Thr Tyr Ser Ala Thr Tyr Asn Pro Asn Gly Asn Ser Tyr Leu Cys
             70                  75                  80

Ile Tyr Gly Trp Ser Thr Asn Pro Leu Val Glu Phe Tyr Ile Val Glu
         85                  90                  95

Ser Trp Gly Asn Trp Arg Pro Pro Gly Ala Thr Ser Leu Gly Gln Val
100                 105                 110                 115

Thr Ile Asp Gly Gly Thr Tyr Asp Ile Tyr Arg Thr Arg Val Asn
                120                 125                 130

Gln Pro Ser Ile Val Gly Thr Ala Thr Phe Asp Gln Tyr Trp Ser Val
             135                 140                 145

Arg Thr Ser Lys Arg Thr Ser Gly Thr Val Thr Val Thr Asp His Phe
             150                 155                 160

Arg Ala Trp Ala Asn Arg Gly Leu Asn Leu Gly Thr Ile Asp Gln Ile
             165                 170                 175

Thr Leu Cys Val Glu Gly Tyr Gln Ser Ser Gly Ser Ala Asn Ile Thr
180                 185                 190                 195

Gln Asn Thr Phe Ser Gln Gly Ser
                200

<210> SEQ ID NO 19
<211> LENGTH: 8603
<212> TYPE: DNA
<213> ORGANISM: artificial sequence
<220> FEATURE:
<223> OTHER INFORMATION: Plasmid pHyGe396 (see Figure 2; example 4).

<400> SEQUENCE: 19
cgcgtagggc cgcggctag  cggccgcgtc gactagaaga gcagagagga cggatttcct      60
gaaggaaatc cgttttttta ttttgcccgt cttataaatt tcgttgtcca actcgcttaa     120
ttgcgagttt ttatttcgtt tatttcaatt aaggtaacta agatcctct  agagtcgatt     180 atgtcttttg cgcagtcggc ttaaaccagt tttcgctggt gcgaaaaaag agtgtcttgt     240
gacactctta aattcaaaat ctatcggtca gatttatacc gatttgattt tatatattct     300
tgaataacat acgccgagtt atcacataaa agcgggaacc aatcatcaaa tttaaacttc     360
attgcataat ccattaaact cttaaattct acgattcctt gttcatcaat aaactcaatc     420
atttctttaa ttaatttata tctatctgtt gttgttttct ttaataattc atcaacatct     480
acaccgccat aaactatcat atcttctttt tgatatttaa attattagg  atcgtccatg     540 tgaagcatat atctcacaag acctttcaca cttcctgcaa tctgcggaat agtcgcattc     600
aattcttctg taattatttt tatctgttca taagatttat taccctcata catcactaga     660
atatgataat gctcttttttt catcctacct tctgtatcag tatccctatc atgtaatgga     720
```

```
gacactacaa attgaatgtg taactctttt aaatactcta accactcggc ttttgctgat      780
tctggatata aaacaaatgt ccaattacgt cctcttgaat ttttcttgtt ttcagtttct      840
tttattacat tttcgctcat gatataataa cggtgctaat acacttaaca aaatttagtc      900
atagataggc agcatgccag tgctgtctat ctttttttgt ttaaaatgca ccgtattcct      960
cctttgcata tttttttatt agaataccgg ttgcatctga tttgctaata ttatattttt     1020
ctttgattct atttaatatc tcattttctt ctgttataag tcttaaagta acagcaactt     1080
ttttctcttc ttttctatct acaaccatca ctgtacctcc caacatctgt ttttttcact     1140
ttaacataaa aaacaacctt taacattaa aaacccaata tttatttatt tgtttggaca      1200
atggacaatg gacacctagg ggggaggtcg tagtaccccc ctatgttttc tcccctaaat     1260
aaccccaaaa atctaagaaa aaaagacctc aaaaaggtct ttaattaaca tctcaaattt     1320
cgcatttatt ccaatttcct ttttgcgtgt gatgcgctgc gtccattaaa aatcctagag     1380
ctttgcaacc gaaagttaat agctgtcgct actactttcg cttacgctct aagtatattt     1440
taaggactgt cacacgcaaa aagttttctc ggcataaaag tacctctaca tctctaaatc     1500
gtctgtacgc tgtttctcac gctttctatc gaccttctgg acattatcct gtacaacatc     1560
cataaactgt cccacacgct cgaatttgga atcattaaag aatttctctt taagcctatt     1620
aaaccctttc tcaaacccag ggaaattcgc cctcgcagca cgatataaag tcactgtact     1680
atcttgaaat ttctctgata cattcaactg ctcattcaaa ctatcattct ctcgctttaa     1740
tttattaacc tctttacttt tttcgtgata cccctctttc catgtattca ctacttcttt     1800
caaactctct ctacgttttt ttaattcttg attttctgtg taatagtctg tgctcttaat     1860
attttcgtaa tcatcaacaa tccgttctgc agaagagatt gtttcttgca ggcgttcaaa     1920
ttcatcagca gttaatatct ttctaccagt ctcttcacgt ccagagaaca aacctgtacg     1980
ctcattttca taatcaaagg gtttcgtaga cctcatatgc tctattccac tctgtaactg     2040
cttatttgcc ttctgtaact catccttaac ttccttgcagt tcctgtttat gaaatacagt     2100
atctttcttg tactgatcca tcgctttatg ttctcgttct gtaacctctt tggacgtgcc     2160
tctttcaagt tcataacctt tctcattcac atactcatta aatctatctt gtaattgagt     2220
aaagtctttc ttgttgccta actgttcttt tgcagacaat ctcccgtcct ctgttaaagg     2280
gacaaaacca aagtgcatat gtgggactct ttcatccaga tggacagtcg catacagcat     2340
attttcctta ccgtattcat tttctagaaa ctccaagcta tctttaaaaa atcgttctat     2400
ttcttctccg cttaaatcat caaagaaatc tttatcactt gtaaccagtc cgtccacatg     2460
tcgaattgca tctgaccgaa ttttacgttt ccctgaataa ttctcatcaa tcgtttcatc     2520
aattttatct ttatacttta tattttgtgc gttaatcaaa tcataatttt tatatgtttc     2580
ctcatgattt atgtctttat tattatagtt tttattctct ctttgattat gtctttgtat     2640
cccgtttgta ttacttgatc ctttaactct ggcaaccctc aaaattgaat gagacatgct     2700
acacctccgg ataataaata tatataaacg tatatagatt tcataaagtc taacacacta     2760
gacttattta cttcgtaatt aagtcgttaa accgtgtgct ctacgaccaa aactataaaa     2820
cctttaagaa ctttcttttt ttacaagaaa aagaaattta gataaatctc tcatatcttt     2880
tattcaataa tcgcatccga ttgcagtata aatttaacga tcactcatca tgttcatatt     2940
tatcagtgct cgtgctataa ttatactaat tttataagga ggaaaaaata tgggcatttt     3000
tagtattttt gtaatcagca cagttcatta tcaaccaaac aaaaaataag tggttataat     3060
gaatcgttaa taagcaaaat tcatataacc aaattaaaga gggttataat gaacgagaaa     3120
```

```
aatataaaac acagtcaaaa ctttattact tcaaaacata atatagataa aataatgaca    3180
aatataagat taaatgaaca tgataatatc tttgaaatcg gctcaggaaa aggccatttt    3240
acccttgaat tagtaaagag gtgtaatttc gtaactgcca ttgaaataga ccataaatta    3300
tgcaaaacta cagaaaataa acttgttgat cacgataatt tccaagtttt aaacaaggat    3360
atattgcagt ttaaatttcc taaaaaccaa tcctataaaa tatatggtaa tataccttat    3420
aacataagta cggatataat acgcaaaatt gttttttgata gtatagctaa tgagatttat    3480
ttaatcgtgg aatacgggtt tgctaaaaga ttattaaata caaaacgctc attggcatta    3540
cttttaatgg cagaagttga tatttctata ttaagtatgg ttccaagaga atattttcat    3600
cctaaaccta aagtgaatag ctcacttatc agattaagta gaaaaaaatc aagaatatca    3660
cacaaagata aacaaaagta taattatttc gttatgaaat gggttaacaa agaatacaag    3720
aaaatattta caaaaaatca atttaacaat tccttaaaac atgcaggaat tgacgattta    3780
aacaatatta gctttgaaca attcttatct cttttcaata gctataaatt atttaataag    3840
taagttaagg gatgcataaa ctgcatccct taacttgttt ttcgtgtgcc tattttttgt    3900
gaatcgacct gcaggcatgc aagcttaagc gagttggaat ttaaatatga tatctacatt    3960
atcagcagta acatcaacct ttgatacaag gttgttgacg attttctttt tattatcata    4020
tgatagttca ttaatcggaa ttgagcccaa ctgagtttta actaactcaa aaacatcagt    4080
agagtcatta aatttattt cgctaatctt agctttaagc agcttttct cagcctgaag    4140 ggaatcagta cgatctttca actcatccat agtgataaaa tcatttaggt acaaatcaga    4200
gttcttttgt attttttat cgatctgtga aatttgcttt ttaaatgacg aagtatcaag    4260
aataggttgg ttgttgccat tgataatttt caataaggag tcattatttt cttgaaatcc    4320
aatcaggttg tcaataacag tatttttcta attacttaaa tcataagttc ctgaatcaca    4380 cttttttattg tcattatata ctgtaattcc ttttgttttt cgaggaaatc tatttgcaca    4440
gtgatatttc atagtgcggc ttccatcttt tcttttgtgg ccaagaacaa tttttaaagg    4500
tgctccacag taaccgcacc ttgccatccc tgacagcata tatttagctt ggaaaggtct    4560
agggttgtta tttctttcat aagtctgctg ttgtctttct tctagctctt tttgaacttt    4620
taaataagtc tcataaggga taattggttt gtgcatacct tcaaataggc tgtccttaaa    4680
tttgatataa ccacagtaaa ctggattatc aagtgtttgt cttagggtac gataagacca    4740
cggtatatct ttaccgatgt gtccagattc attgagttta tctcttaatt ttgtaagtga    4800
tattcctgat aaaataatcag tgaatatttg ttcaactatt gtagcttgta aaggaacaat    4860
ttctaatata cctgtctttc tgttgtggta atacccaaaa gctgtcttag tccacatcat    4920
agacttacca gatttcgctc gccctagttt acccatagtc atgcgttctt ttatattctc    4980
tctttcaaac tcattaattg cagaaagaat agtgagaaac aagctaccca tagcagaaga    5040
agtatcaata ctttcattaa gcgagataaa gtctatttta ttttttgtga acacatcctt    5100
aacaagataa agagtatctc ttacactacg tgaaaggcgg tctagcttat atacaagaac    5160
tgtatcaaaa gctttattct cgatatcgtt gattaatctt tgcattgctg ggcgttcaag    5220
tttggcccct gaaaaaccag catcagtata agtatcagat acttgccacc ccattgcttc    5280
agcatatttt gttaaacggt caatttgctc atcaattgag aacccttcct ctgcttggtt    5340
agtagtggat actcgtgtat agattgctac ttcttagtc atgagatttc ccccttaaaa    5400
ataaattcat tcaaatacag atgcatttta tttcatatag taagtacatc acctattagt    5460
```

```
ttgttgttta aacaaactaa cttatttca tcttatatag cctcgtcagt attttcaata    5520
ttttttttag ttttttatga acacattaga tataataaag ggaagattcg ctatgtacta    5580
tgttgatact taatttaaag attaaacaaa tggagtggat gaagtggata tcgctgatca    5640
aacctttgtc aaaaaagtaa atcaaaagtt attattaaaa gaaatcctta aaaattcacc    5700
tatttcaaga gcaaaattat ctgaaatgac tggattaaat aaatcaactg tctcatcaca    5760
ggtaaacacg ttaatgaaag aaagtatggt atttgaaata ggtcaaggac aatcaagtgg    5820
cggaagaaga cctgtcatgc ttgttttaa taaaaaggca ggatactccg ttggaataga    5880
tgttggtgtg gattatatta atggcatttt aacagacctt gaaggaacaa tcgttcttga    5940
tcaataccgc catttggaat ccaattctcc agaaataacg aaagacattt tgattgatat    6000
gattcatcac tttattacgc aaatgcccca atctccgtac gggcttattg gtataggtat    6060
ttgcgtgcct ggactcattg ataaagatca aaaaattgtt ttcactccga actccaactg    6120
gagagatatt gacttaaaat cttcgataca agagaagtac aatgtgcctg ttttttattga    6180 aaatgaggca aatgctggcg catatggaga aaaagtattt ggagctgcaa aaaatcacga    6240
taacattatt tacgtaagta tcagcacagg aatagggatc ggtgttatta tcaacaatca    6300
tttatataga ggagtaagcg gcttctctgg agaaatggga catatgacaa tagacttaa    6360 tggtcctaaa tgcagttgcg gaaaccgagg atgctgggaa ttgtatgctt cagagaaggc    6420
tttattaaaa tctcttcaga ccaaagagaa aaaactgtcc tatcaagata tcataaacct    6480
cgcccatctg aatgatatcg gaaccttaaa tgcattacaa aattttggat tctatttagg    6540
aataggcctt accaatattc taaatacttt caacccacaa gccgtaattt taagaaatag    6600
cataattgaa tcgcatccta tggttttaaa ttcaatgaga agtgaagtat catcaagggt    6660
ttattcccaa ttaggcaata gctatgaatt attgccatct tccttaggac agaatgcacc    6720
ggcattagga atgtcctcca ttgtgattga tcattttctg acatgattaa caatgtaatt    6780
ttttatggaa tggacagctc atctttaaag atgagttttt ttattctagg agtatttctg    6840
aattcgtgct cattattaat ctgttcagca atcgggcgcg attgctgaat aaaagatacg    6900
agagacctct cttgtatctt ttttattttg agtggttttg tccgttacac tagaaaaccg    6960
aaagacaata aaaattttat tcttgctgag tctggctttc ggtaagctag acaaaacgga    7020
caaaataaaa attggcaagg gtttaaaggt ggagattttt tgagtgatct tctcaaaaaa    7080
tactacctgt cccttgctga ttttaaacg agcacgagag caaaaccccc ctttgctgag    7140
gtggcagagg gcaggttttt ttgtttcttt tttctcgtaa aaaaaagaaa ggtcttaaag    7200
gttttatggt tttggtcggc actgccgaca gcctcgcaga gcacacactt tatgaatata    7260
aagtatagtg tgttatactt tacttggaag tggttgccgg aaagagcgaa aatgcctcac    7320
attaaagata atatctttga attgtaacgc ccctcaaaag taagaactac aaaaaaagaa    7380
tacgttatat agaaatatgt ttgaaccttc ttcagattac aaatatattc ggacggactc    7440
tacctcaaat gctatctaa ctatagaatg acatacaagc acaaccttga aaatttgaaa    7500
atataactac caatgaactt gttcatgtga attatcgctg tatttaattt tctcaattca    7560
atatataata tgccaataca ttgttacaag tagaaattaa gacaccctg atagccttac    7620 tatacctaac atgatgtagt attaaatgaa tatgtaaata tatttatgat aagaagcgac    7680
ttatttataa tcattacata tttttctatt ggaatgatta agattccaat agaatagtgt    7740
ataaattatt tatcttgaaa ggagggatgc ctaaaaacga agaacattaa aaacatatat    7800
ttgcaccgtc taatggattt atgaaaaatc attttatcag tttgaaaatt atgtattatg    7860
```

```
gagctcggta ccctatgttt cacattgaaa ggggaggaga atcatgaaac aacaaaaacg    7920
gctttacgcc cgattggtgc ttatgtgcac gctgttattt gtcagtttgc cgattacaaa    7980
aacatcagcc cagacatcaa tcacacttac atctaacgca tcaggcacat tcgacggcta    8040
ttactacgag ctttggaagg acacaggcaa cacgactatg actgtataca ctcaaggtcg    8100
cttctcatgc cagtggtcta acatcaacaa cgcgcttttc cgcacgggca agaagtacaa    8160
ccagaactgg caatctcttg gcactatccg catcacttat tctgcgacat acaacccgaa    8220
cggcaactct tacctttgta tctacggctg gtctacgaac ccgcttgttg agttctacat    8280
cgtagagtct tggggcaact ggcgtcctcc tggcgcaaca tctcttggcc aggttacaat    8340
cgatggtggc acatatgaca tctaccgcac tactcgcgtt aaccagccta gcatcgttgg    8400
cacagctact ttcgaccaat actggagcgt tcgcactagc aagcgcacat ctggcacagt    8460
tacggttacg gaccactttc gcgcatgggc aaatcgtggc cttaaccttg gcacaatcga    8520
ccaaatcaca ctttgtgttg agggctacca gtcttctggc agcgcaaaca tcactcaaaa    8580
cactttctct cagggcagct aaa                                           8603
```

EXPRESSION OF NATIVELY SECRETED POLYPEPTIDES WITHOUT SIGNAL PEPTIDE

CROSS-REFERENCE TO RELATED APPLICATIONS

This application is a 35 U.S.C. 371 national application of international application no. PCT/EP2014/062815 filed Jun. 18, 2014, which claims priority or the benefit under 35 U.S.C. 119 of European application no. 13173651.4 filed Jun. 25, 2013. The content of each application is fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to methods of recombinantly producing a natively secreted polypeptide, the method comprising the steps of providing a microorganism host cell comprising an exogenous polynucleotide encoding a natively secreted polypeptide without a translationally fused signal peptide; cultivating the microorganism host cell under conditions conducive to the expression of the polypeptide and, optionally, recovering the polypeptide, as well as microorganisms, certain polynucleotides, expression constructs and protease substitution variants.

BACKGROUND OF THE INVENTION

A thermostable secreted protease denoted PfuS was isolated from *Pyrococcus furiosus* and has previously been produced using an expression DNA construct including a secretion signal but yields of the PfuS protease were rather low (EP0994191A1; Takara, JP). It is of interest to increase the expression yields of the thermostabile PfuS protease from *Pyrococcus furiosus*, so that it can be produced in sufficient quantities and at an acceptable production economy in order for the enzyme to be employed industrially.

A thermostable secreted xylanase denoted XynB was identified and cloned from *Dictyoglomus thermophilum*, the enzyme was recombinantly expressed in *E. coli*. The mature N terminus of XynB was located downstream of a 23-amino-acid leader peptide, as predicted by the SignalP signal peptide analysis software and supported by the results of a multiple sequence analysis performed with other bacterial family 11 xylanases. The XynB leader peptide made the enzyme toxic for *E. coli*. The XynB enzyme was expressed in *E. coli* without leader peptide and recovered by cell lysis (Morris D D et al. 1998, Appl. Environ. Microbiol. 64 (5): 1759-65). The XynB enzyme was also expressed recombinantly in a *Bacillus subtilis* host with its native secretion signal but only in very low yields (Zhang et al; Appl Biochem Biotechnol (2010) 160:1484-1495). It is of interest to increase the expression yields of the thermostabile XynB xylanase from *Dictyoglomus thermophilum*, so that it can be produced in sufficient quantities and at an acceptable production economy in order for the enzyme to be employed industrially.

*Bacillus* host cells have been characterized as workhorses in the industrial manufacture of various polypeptides of interest, mainly because they actively secrete polypeptides that have a so-called signal peptide. The signal peptide is a small polypeptide, typically around 20-30 amino acids, that is expressed in transcriptional and translational fusion with the N-terminal of a polypeptide to be secreted. It directs the fused polypeptide into the secretory machinery of a suitably equipped host cell, whereupon the fused polypeptide is cleaved while the now-matured polypeptide of interest is secreted into the surrounding culture broth without its signal peptide which is retained in the cell and degraded.

The secretion of recombinantly produced polypeptides of interest in *Bacillus* enables a comparatively easy recovery of the polypeptides directly from the culture broth without having to perform a cell lysis step. Only polypeptides destined to be exported from the cell into the growth medium are natively outfitted with a signal peptide in *Bacillus*.

Most polypeptides in a cell are not destined for export but are instead intended to be intracellular, periplasmic, membrane-bound etc. Such natively non-secreted polypeptides are usually considered burdensome to produce because they either need to be recovered from within the host cells which usually requires a messy cell-lysis step resulting in a challenging recovery process which, in turn, is why natively secreted enzymes are preferred for industrial manufacture.

SUMMARY OF THE INVENTION

In order to investigate the expression levels of the PfuS protease and the XynB xylanase (without the native C-terminal cellulose-binding domain) in *Bacillus*, the two enzymes were expressed as translational N-terminal fusion polypeptide with a well-known effective *Bacillus* signal peptide. However, the enzymes were also expressed experimentally in *Bacillus* hosts without any signal peptide whatsoever.

Contrary to expectations, we found comparatively high yields of the two enzymes in the supernatants when the enzymes were expressed without any secretion signal peptide, as demonstrated in the examples herein. This is a highly surprising result and one of economic significance, because it demonstrates that PfuS-like proteases and XynB-like xylanases can be produced in *Bacillus* without a signal peptide and with higher yields than if a signal peptide had been employed. The enzymes can successfully be recovered directly from the broth without a costly cell lysis step.

Accordingly, in a first aspect the invention relates to methods of recombinantly producing a natively secreted polypeptide, the method comprising the steps of:
a) providing a microorganism host cell comprising an exogenous polynucleotide encoding a natively secreted polypeptide without a translationally fused signal peptide;
b) cultivating the microorganism host cell under conditions conducive to the expression of the polypeptide and, optionally,
 recovering the polypeptide.

In a second aspect, the invention relates to a recombinant microorganism host cell comprising an exogenous polynucleotide encoding a natively secreted polypeptide without a translationally fused signal peptide.

A third aspect of the invention relates to an isolated synthetic polynucleotide encoding a natively secreted polypeptide without a translationally fused signal peptide, wherein said polypeptide is a protease having an amino acid sequence at least 80% identical to the sequence shown in positions 1 to 413 of SEQ ID NO:8, preferably at least 85%, at least 90%, at least 91%, at least 92%, at least 93%, at least 94%, at least 95%, at least 96%, at least 97%, at least 98%, at least 99%, or 100% identical to the sequence shown in positions 1 to 413 of SEQ ID NO:8; OR a xylanase having an amino acid sequence at least 80% identical to the sequence shown in positions 1 to 204 of SEQ ID NO:15, preferably at least 85%, at least 90%, at least 91%, at least 92%, at least 93%, at least 94%, at least 95%, at least 96%, at least 97%, at least 98%, at least 99%, or 100% identical to the sequence shown in positions 1 to 204 of SEQ ID NO:15.

In a fourth aspect, the invention relates to a nucleic acid construct or an expression vector comprising a polynucleotide as defined in any of claims 11 to 14 operably linked to control sequences that provide for its expression in a host cell of choice.

A fifth aspect of the invention relates to an isolated synthetic polypeptide, said polypeptide being:

a) a protease having, comprising or consisting of an amino acid sequence at least 80% identical to the protease shown in positions 1 to 413 of SEQ ID NO: 6, preferably at least 85%, at least 90%, at least 91%, at least 92%, at least 93%, at least 94%, at least 95%, at least 96%, at least 97%, at least 98%, at least 99%, or 100% identical to the sequence shown in positions 1 to 413 of SEQ ID NO: 6, wherein the protease comprises an amino acid substitution in a position corresponding to position 369 in SEQ ID NO:6; preferably a glycine in a position corresponding to position 369 in SEQ ID NO:6 is substituted for an aspartic acid: G369D; OR b) a xylanase having, comprising or consisting of an amino acid sequence at least 80% identical to the protease shown in positions 1 to 204 of SEQ ID NO:15, preferably at least 85%, at least 90%, at least 91%, at least 92%, at least 93%, at least 94%, at least 95%, at least 96%, at least 97%, at least 98%, at least 99%, or 100% identical to the sequence shown in positions 1 to 204 of SEQ ID NO:15 and comprising a methionine as its first N-terminal amino acid.

A sixth aspect of the invention relates to an isolated synthetic polypeptide, said polypeptide being:

a) a protease having the amino acid sequence or comprising or consisting of the amino acid sequence shown in positions 1 to 413 of SEQ ID NO:8; OR b) a xylanase having the amino acid sequence or comprising or consisting of the amino acid sequence shown in positions 1 to 204 of SEQ ID NO:15 and comprising a methionine as its first N-terminal amino acid.

A final aspect relates to a composition comprising a protease polypeptide as defined in the fifth or sixth aspects.

DEFINITIONS

Figure 1:
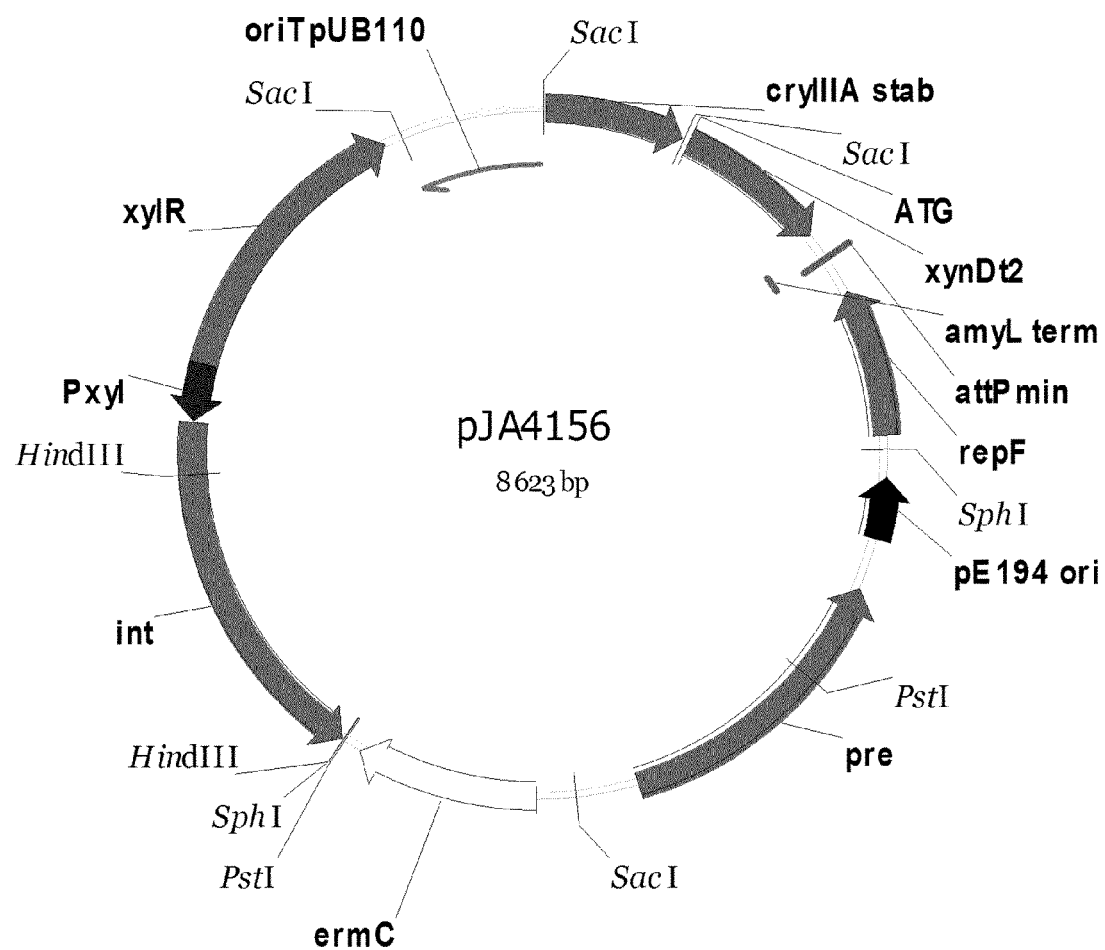
FIG. 1 shows a plasmid map of the pJA4156 plasmid from Example 4.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Mature polypeptide: The term "mature polypeptide" means a polypeptide in its final form following translation and any post-translational modifications, such as N-terminal processing, C-terminal truncation, etc. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Full-length polypeptide: The term "full-length polypeptide" is defined herein as a precursor form of a polypeptide having biological activity, wherein the precursor contains a signal peptide and alternatively also a propeptide, wherein upon secretion from a cell, the signal peptide is cleaved and alternatively also the propeptide is cleaved yielding a polypeptide with biological activity.

Signal peptide: The term "signal peptide" is defined herein as a peptide linked (fused) in frame to the amino terminus of a polypeptide having biological activity and directs the polypeptide into the cell's secretory pathway. A propeptide may be present between the signal peptide and the amino terminus of the polypeptide (see prepropeptide definition below).

Propeptide: The term "propeptide" is an amino acid sequence linked (fused) in frame to the amino terminus of a polypeptide, wherein the resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide.

Prepropeptide: The term "prepropeptide" is defined herein as a signal peptide and propeptide present at the amino terminus of a polypeptide, where the propeptide is linked (or fused) in frame to the amino terminus of a polypeptide and the signal peptide region is linked in frame (or fused) to the amino terminus of the propeptide region.

Signal peptide coding sequence: The term "signal peptide coding sequence" is defined herein as a polynucleootide that encodes a signal peptide.

Propeptide coding sequence: The term "propeptide coding sequence" is defined herein as a polynucleootide that encodes a propeptide.

Prepropeptide coding sequence: The term "prepropeptide coding sequence" is defined herein as a polynucleootide that encodes a prepropeptide.

Wild-type signal peptide: The term "wild-type signal peptide" denotes a signal peptide expressed by a naturally occurring microorganism, such as a yeast or filamentous fungus found in nature.

Parent signal peptide: The term "parent signal peptide" as used herein means a signal peptide to which modifications, e.g., substitution(s), insertion(s), deletion(s), and/or truncation(s), are made to produce a signal peptide variant of the present invention. This term also refers to the signal peptide with which a variant is compared and aligned. The parent may be a naturally occurring (wild-type) signal peptide, or it may even be a variant thereof, prepared by any suitable means. For instance, the parent signal peptide may be a variant of a naturally occurring signal peptide which has been modified or altered in the amino acid sequence. A parent signal peptide may also be an allelic variant which is a signal peptide encoded by any of two or more alternative forms of a polynucleotide sequence occupying the same chromosomal locus.

Wild-type prepropeptide: The term "wild-type prepropeptide" denotes a prepropeptide expressed by a naturally occurring microorganism, such as a yeast or filamentous fungus found in nature.

Parent prepropeptide: The term "parent prepropeptide" as used herein means a prepropeptide to which modifications, e.g., substitution(s), insertion(s), deletion(s), and/or truncation(s), are made to produce a prepropeptide variant of the present invention. This term also refers to the prepropeptide with which a variant is compared and aligned. The parent may be a naturally occurring (wild-type) prepropeptide, or it may even be a variant thereof, prepared by any suitable means. For instance, the parent prepropeptide may be a variant of a naturally occurring prepropeptide which has been modified or altered in the amino acid sequence. A parent prepropeptide may also be an allelic variant which is a prepropeptide encoded by any of two or more alternative forms of a polynucleotide sequence occupying the same chromosomal locus.

Variant: The term "variant" is defined herein as a peptide or polypeptide comprising one or more (several) alterations, such as substitutions, insertions, deletions, and/or truncations of one or more (several) specific amino acid residues at one or more (several) specific positions in the peptide or polypeptide.

Variant signal peptide: The term "variant signal peptide" is defined herein as a signal peptide of a parent signal peptide, wherein the variant signal peptide comprises one or more (several) alterations, such as substitutions, insertions, deletions, and/or truncations of one or more (several) specific amino acid residues at one or more (several) specific positions in the signal peptide.

Variant prepropeptide: The term "variant prepropeptide" is defined herein as a prepropeptide of a parent prepropeptide, wherein the variant prepropeptide comprises one or more (several) alterations, such as substitutions, insertions, deletions, and/or truncations of one or more (several) specific amino acid residues at one or more (several) specific positions in the prepropeptide. Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment−Total Number of Gaps in Alignment)

Variant: The term "variant" means a polypeptide having enzyme activity comprising an alteration, i.e., a substitution, insertion, and/or deletion, at one or more (e.g., several) positions compared to the amino acid sequence of its parent wildtype or reference. A substitution means replacement of the amino acid occupying a position with a different amino acid; a deletion means removal of the amino acid occupying a position; and an insertion means adding an amino acid adjacent to and immediately following the amino acid occupying a position.

Variants of a mature polypeptide may comprise a substitution, deletion, and/or insertion at one or more (e.g., several) positions. The number of amino acid substitutions, deletions and/or insertions introduced into the mature polypeptide may be up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, N.Y. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for enzyme activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Fusion polypeptides: The polypeptide of interest may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

DETAILED DESCRIPTION OF THE INVENTION

Polynucleotides

The present invention relates to isolated synthetic polynucleotides encoding a natively secreted protease or xylanase with no secretion signal, said polypeptide being a protease having, comprising or consisting of an amino acid sequence at least 80% identical to the sequence shown in positions 1 to 413 of SEQ ID NO:8; preferably at least 85%, at least 90%, at least 91%, at least 92%, at least 93%, at least 94%, at least 95%, at least 96%, at least 97%, at least 98%, at least 99%, or 100% identical to the protease shown in positions 1 to 413 of SEQ ID NO:8; OR said polypeptide being a xylanase having, comprising or consisting of an amino acid sequence at least 80% identical to the sequence shown in positions 1 to 413 of SEQ ID NO:8; preferably at least 85%, at least 90%, at least 91%, at least 92%, at least 93%, at least 94%, at least 95%, at least 96%, at least 97%, at least 98%, at least 99%, or 100% identical to the protease shown in positions 1 to 204 of SEQ ID NO:15.

In a preferred embodiment, the polynucleotide of the invention has, comprises or consists of a nucleotide sequence at least 80% identical to the sequence shown in positions 1 to 1569 of SEQ ID NO:7; preferably at least 85%, at least 90%, at least 91%, at least 92%, at least 93%, at least 94%, at least 95%, at least 96%, at least 97%, at least 98%, at least 99%, or 100% identical to the sequence shown in positions 1 to 1569 of SEQ ID NO:7; more preferably the polynucleotide of the invention has, comprises or consists of a nucleotide sequence at least 80% identical to the sequence shown in positions 331 to 1569 of SEQ ID NO:7; still more preferably at least 85%, at least 90%, at least 91%, at least 92%, at least 93%, at least 94%, at least 95%, at least 96%, at least 97%, at least 98%, at least 99%, or 100% identical to the sequence shown in positions 331 to 1569 of SEQ ID NO:7.

In another preferred embodiment, the polynucleotide of the invention has, comprises or consists of a nucleotide sequence at least 80% identical to the sequence shown in positions 1 to 612 of SEQ ID NO:14, preferably at least 85%, at least 90%, at least 91%, at least 92%, at least 93%, at least 94%, at least 95%, at least 96%, at least 97%, at least 98%, at least 99%, or 100% identical to the sequence shown in positions 1 to 612 of SEQ ID NO:14.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, PCR: A Guide to Methods and Application, Academic Press, N.Y. Other nucleic acid amplification procedures such as ligase chain reaction (LCR), ligation activated transcription (LAT) and polynucleotide-based amplification (NASBA) may be used. The polynucleotides may be cloned from a strain of *Pyrococcus*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Sources of Polynucleotides

A polynucleotide encoding a protease of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted.

The polynucleotide may be a bacterial polynucleotide. For example, the polynucleotide may be a Gram-positive bacterial polynucleotide such as a *Bacillus, Clostridium, Enterococcus, Geobacillus, Lactobacillus, Lactococcus, Oceanobacillus, Staphylococcus, Streptococcus,* or *Streptomyces* polynucleotide encoding a secreted polypeptide having protease activity, or a Gram-negative bacterial polynucleotide such as a *Campylobacter, E. coli, Flavobacterium, Fusobacterium, Helicobacter, Ilyobacter, Neisseria, Pseudomonas, Salmonella,* or *Ureaplasma* polynucleotide.

In one aspect, the polynucleotide of the invention is from an extreme thermophile anaerobic bacterium, such as, from the *Dictyoglomi* phylum, including *Dictyoglomus thermophilum*.

In another aspect, the polynucleotide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polynucleotide.

In another aspect, the polynucleotide is a *Streptococcus equisimilis, Streptococcus pyogenes, Streptococcus uberis,* or *Streptococcus equi* subsp. *Zooepidemicus* polynucleotide.

In another aspect, the polynucleotide is a *Streptomyces achromogenes, Streptomyces avermitilis, Streptomyces coelicolor, Streptomyces griseus,* or *Streptomyces lividans* polynucleotide.

In another aspect, the polynucleotide is a *Pyrococcus* polynucleotide; preferably a *Pyrococcus furiosus* polynucleotide.

The polynucleotide may be a fungal polynucleotide. For example, the polynucleotide may be a yeast polynucleotide such as a *Candida, Kluyveromyces, Pichia, Saccharomyces, Schizosaccharomyces,* or *Yarrowia* polypeptide; or a filamentous fungal polypeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polynucleotide.

In another aspect, the polynucleotide is a *Saccharomyces carlsbergensis, Saccharomyces cerevisiae, Saccharomyces*

*diastaticus*, *Saccharomyces douglasii*, *Saccharomyces kluyveri*, *Saccharomyces norbensis*, or *Saccharomyces oviformis* polynucleotide.

In another aspect, the polynucleotide is an *Acremonium cellulolyticus*, *Aspergillus aculeatus*, *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia setosa*, *Thielavia spededonium*, *Thielavia subthermophila*, *Thielavia terrestris*, *Trichoderma harzianum*, *Trichoderma koningii*, *Trichoderma longibrachiatum*, *Trichoderma reesei*, or *Trichoderma viride* polynucleotide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polynucleotide may be identified and obtained from other sources including microorganisms isolated from nature (e.g., soil, composts, water, etc.) or DNA samples obtained directly from natural materials (e.g., soil, composts, water, etc.). Techniques for isolating microorganisms and DNA directly from natural habitats are well known in the art. A polynucleotide may then be obtained by similarly screening a genomic DNA or cDNA library of another microorganism or mixed DNA sample. Once a polynucleotide has been detected, the polynucleotide can be isolated or cloned by utilizing techniques that are known to those of ordinary skill in the art (see, e.g., Sambrook et al., 1989, supra).

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell. In some aspects, the promoter is a heterologous promoter.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. Other examples of regulatory sequences are those that allow for gene amplification.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention, wherein said host cell is capable of producing the polypeptide of the invention.

A construct or vector comprising a polynucleotide is introduced into a host cell so that the construct or vector is maintained as a chromosomal integrant or as a self-replicating extrachromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be bacterial, for example, it may be prokaryotic, preferably any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The prokaryotic host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus* megaterium, *Bacillus pumilus, Bacillus stearothermophilus, Bacillus subtilis*, and *Bacillus thuringiensis* cells.

The host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (*Praha*) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

In a preferred embodiment of the second aspect of the invention, a recombinant microorganism host cell comprises an exogenous polynucleotide encoding a natively secreted polypeptide without a translationally fused signal peptide.

Preferably, the microorganism host cell is a prokaryotic host cell, preferably a Gram-positive host cell, more preferably a *Bacillus* host cell and most preferably the host cell is selected from the group consisting of *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis*.

It is preferred that the polypeptide is a homologous or heterologous enzyme, preferably the enzyme is selected from the group consisting of hydrolase, isomerase, ligase, lyase, oxidoreductase, or transferase; more preferably the enzyme is an alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or a xylanase.

Further, it is preferable that the polypeptide is:

a) a protease polypeptide comprising or consisting of an amino acid sequence at least 80% identical to the sequence shown in positions 1 to 413 of SEQ ID NO:8, preferably at least 85%, at least 90%, at least 91%, at least 92%, at least 93%, at least 94%, at least 95%, at least 96%, at least 97%, at least 98%, at least 99%, or 100% identical to the sequence shown in positions 1 to 413 of SEQ ID NO:8; OR b) a xylanase polypeptide comprising or consisting of an amino acid sequence at least 80% identical to the sequence shown in positions 1 to 204 of SEQ ID NO:15, preferably at least 85%, at least 90%, at least 91%, at least 92%, at least 93%, at least 94%, at least 95%, at least 96%, at least 97%, at least 98%, at least 99%, or 100% identical to the sequence shown in positions 1 to 204 of SEQ ID NO:15.

Still more preferable, the polypeptide is:

a) a protease encoded by a polynucleotide comprising or consisting of a nucleotide sequence at least 80% identical to the sequence shown in positions 1 to 1569 of SEQ ID NO:7, preferably at least 85%, at least 90%, at least 91%, at least 92%, at least 93%, at least 94%, at least 95%, at least 96%, at least 97%, at least 98%, at least 99%, or 100% identical to the sequence shown in positions 1 to 1569 of SEQ ID NO:7; OR preferably at least 80% identical to the sequence shown in positions 331 to 1569 of SEQ ID NO:7, preferably at least 85%, at least 90%, at least 91%, at least 92%, at least 93%, at least 94%, at least 95%, at least 96%, at least 97%, at least 98%, at least 99%, or 100% identical to the sequence shown in positions 331 to 1569 of SEQ ID NO:7, OR b) a xylanase encoded by a polynucleotide comprising or consisting of a nucleotide sequence at least 80% identical to the sequence shown in positions 1 to 612 of SEQ ID NO:14, preferably at least 85%, at least 90%, at least 91%, at least 92%, at least 93%, at least 94%, at least 95%, at least 96%, at least 97%, at least 98%, at least 99%, or 100% identical to the sequence shown in positions 1 to 612 of SEQ ID NO:14.

Methods of Production

The present invention also relates to methods of of recombinantly producing a natively secreted polypeptide, the method comprising the steps of:

a) providing a microorganism host cell comprising an exogenous polynucleotide encoding a natively secreted polypeptide without a translationally fused signal peptide;

b) cultivating the microorganism host cell under conditions conducive to the expression of the polypeptide and, optionally, recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, N.Y., 1989) to obtain substantially pure polypeptides.

In an alternative aspect, the polypeptide is not recovered, but rather a host cell of the present invention expressing the polypeptide is used as a source of the polypeptide.

Preferably the microorganism is a prokaryotic host cell, preferably a Gram-positive host cell, more preferably a *Bacillus* host cell and most preferably the host cell is selected from the group consisting of *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis.*

It is preferred that the polypeptide is a homologous or heterologous enzyme, preferably the enzyme is selected from the group consisting of hydrolase, isomerase, ligase, lyase, oxidoreductase, or transferase; more preferably the enzyme is an alpha-galactosidase, alpha-glucosidase, glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or a xylanase.

In a preferred method of the first aspect, the polypeptide is:
a) a protease polypeptide comprising or consisting of an amino acid sequence at least 80% identical to the sequence shown in positions 1 to 413 of SEQ ID NO:8, preferably at least 85%, at least 90%, at least 91%, at least 92%, at least 93%, at least 94%, at least 95%, at least 96%, at least 97%, at least 98%, at least 99%, or 100% identical to the sequence shown in positions 1 to 413 of SEQ ID NO:8, OR
b) a xylanase polypeptide comprising or consisting of an amino acid sequence at least 80% identical to the sequence shown in positions 1 to 204 of SEQ ID NO:15, preferably at least 85%, at least 90%, at least 91%, at least 92%, at least 93%, at least 94%, at least 95%, at least 96%, at least 97%, at least 98%, at least 99%, or 100% identical to the sequence shown in positions 1 to 204 of SEQ ID NO:15.

In another preferred embodiment of the first aspect, the polypeptide is:
a) a protease encoded by a polynucleotide comprising or consisting of a nucleotide sequence at least 80% identical to the sequence shown in positions 1 to 1569 of SEQ ID NO:7, preferably at least 85%, at least 90%, at least 91%, at least 92%, at least 93%, at least 94%, at least 95%, at least 96%, at least 97%, at least 98%, at least 99%, or 100% identical to the sequence shown in positions 1 to 1569 of SEQ ID NO:7; OR preferably at least 80% identical to the sequence shown in positions 331 to 1569 of SEQ ID NO:7, preferably at least 85%, at least 90%, at least 91%, at least 92%, at least 93%, at least 94%, at least 95%, at least 96%, at least 97%, at least 98%, at least 99%, or 100% identical to the sequence shown in positions 331 to 1569 of SEQ ID NO:7; OR
b) a xylanase encoded by a polynucleotide comprising or consisting of a nucleotide sequence at least 80% identical to the sequence shown in positions 1 to 612 of SEQ ID NO:14, preferably at least 85%, at least 90%, at least 91%, at least 92%, at least 93%, at least 94%, at least 95%, at least 96%, at least 97%, at least 98%, at least 99%, or 100% identical to the sequence shown in positions 1 to 612 of SEQ ID NO:14.

Polypeptides Having Protease Activity

In a preferred embodiment, the isolated synthetic protease polypeptide having, comprising or consisting of an amino acid sequence at least 80% identical to the protease shown in positions 1 to 413 of SEQ ID NO: 6, preferably at least 85%, at least 90%, at least 91%, at least 92%, at least 93%, at least 94%, at least 95%, at least 96%, at least 97%, at least 98%, at least 99%, or 100% identical to the sequence shown in positions 1 to 413 of SEQ ID NO: 6, wherein the protease comprises an amino acid substitution in a position corresponding to position 369 in SEQ ID NO:6; preferably a glycine in a position corresponding to position 369 in SEQ ID NO:6 is substituted for an aspartic acid: G369D.

In an embodiment, the present invention relates to an isolated synthetic protease polypeptide having, comprising or consisting of the amino acid sequence shown in positions 1 to 413 of SEQ ID NO:8, or a fragment thereof having protease activity.

In a preferred embodiment, the isolated synthetic protease polypeptide of the invention is a substitution variant of the mature PfuS protease shown in positions 1 to 413 of SEQ ID NO:6, wherein the glycine in position 369 is substituted for an aspartic acid: G369D.

Polypeptides Having Xylanase Activity

In a preferred embodiment, the isolated synthetic polypeptide of the invention is a xylanase having, comprising or consisting of an amino acid sequence at least 80% identical to the protease shown in positions 1 to 204 of SEQ ID NO:15, preferably at least 85%, at least 90%, at least 91%, at least 92%, at least 93%, at least 94%, at least 95%, at least 96%, at least 97%, at least 98%, at least 99%, or 100% identical to the sequence shown in positions 1 to 204 of SEQ ID NO:15, and comprising a methionine as its first N-terminal amino acid.

In an embodiment, the present invention relates to an isolated synthetic xylanase polypeptide having, comprising or consisting of the amino acid sequence shown in positions 1 to 204 of SEQ ID NO:15, or a fragment thereof having xylanase activity, and comprising a methionine as its first N-terminal amino acid.

In a preferred embodiment, the isolated synthetic protease polypeptide of the invention is a substitution variant of the mature PfuS protease shown in positions 1 to 413 of SEQ ID NO:6, wherein the glycine in position 369 is substituted for an aspartic acid: G369D.

Enzyme Compositions

The present invention also relates to compositions comprising a specific protease polypeptide of the present invention. Preferably, the compositions are enriched in such a polypeptide. The term "enriched" indicates that the protease activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of hydrolase, isomerase, ligase, lyase, oxidoreductase, or transferase; more preferably the enzyme is an alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or a xylanase.

Additional compositions suitable with the protease of the present invention are described in WO2013/082486, the content of which is incorporated herein by reference.

The compositions may be prepared in accordance with methods known in the art and may be in the form of a liquid or a dry composition. The compositions may be stabilized in accordance with methods known in the art.

In a preferred embodiment, the invention relates to a composition comprising a protease polypeptide as defined in the above section entitled "Polypeptides Having Protease Activity".

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

The following examples are provided by way of illustration and are not intended to be limiting of the invention.

EXAMPLES

Example 1 Cloning and Expression of PfuS Protease from *Pyrococcus furiosus* ATCC 43587/DSM 3638

The protease PfuS from *Pyrococcus furiosus* has been described as a thermostable protease (Appl. Environ. Microbiol., 56:1992-1998 (1990); FEMS Microbiol. Letters, 71:17-20 (1990); J. Gen. Microbiol., 137:1193-1199 (1991)). Recombinant expression of the PfuS protease has previously been shown in the *Bacillus subtilis* host organism, but expression levels were very low (EP0994191 A1; Takara (JP)).

Herein we describe a new method of producing the PfuS protease enzyme using a recombinant cloning and expression construct that lacks the native signal peptide of PfuS or any other signal peptide. A surprisingly high enzyme yield was obtained when expressing this construct in a *Bacillus* host cell.

The native PfuS protease-encoding DNA sequence is shown in SEQ ID NO:1 and the amino acid sequence of the PfuS protease is shown in SEQ ID NO:2 (UNIPROT: Q8U0C9).

A synthetic coding sequence was designed based on the amino acid sequence of PfuS. The codon usage in the synthetic gene was optimized for *Bacillus subtilis* expression, as described earlier in WO12025577.

DNA was amplified from the synthetic DNA by PCR using the following primer pair under standard conditions:
forward primer: aaaggagaggataaagaatggcacctgagaagaaa (SEQ ID NO:3)
reverse primer: gcgttttttattgattaacgcgtttatggtgatgagccaggc (SEQ ID NO:4)

Judged by agarose gel electrophoresis the resulting PCR fragment had the expected size of 1631 bp. The PCR fragment was purified before a second PCR reaction (PCR2) was made. In this PCR2 reaction, the 5' end of the PCR1 fragment was fused and operably linked to a DNA fragment containing a triple promoter disclosed in WO 9943835. A DNA fragment encoding a chloramphenicol acetyltransferase was fused to the 3' end of the PCR1 product. The chloramphenicol acetyltransferase genes was used as an antibiotic maker (as described in Diderichsen et al., 1993, Plasmid 30: 312-315). The intended final PfuS-encoding DNA fragment obtained is shown in SEQ ID NO:5 and the intended encoded amino acid sequence is shown in SEQ ID NO:6.

Alternatively to the PCR reactions described above, the complete DNA fragment including all regulatory elements can be ordered as synthetic DNA by commercial vendors.

The expression construct of SEQ ID NO:5 was integrated into the *B. subtilis* genome by homologous recombinantion as described in WO 99/43835. The expression host was a *B. subtilis* strain with the following phenotype: not sporulating (spo−), biotin auxotroph (biol−), protease negative (NprE− and AprE−), alpha-amylase negative (AmyE−), not surfactin producing (SrfC−).

One *B. subtilis* chloramphenicol resistant expression clone denoted MTBO0411-1 was selected on a TB agar plate containing chloramphenicol as selection marker. The clone was cultivated in liquid media on a rotary shaking table in 500 mL baffled Erlenmeyer flasks each containing 100 ml casein based media supplemented with 34 mg/l chloramphenicol.

DNA sequencing was employed to verify the polynucleotide insert from the selected clone and a random mutation was identified in position 1463 of SEQ ID NO:5, where the sequence had changed from G to A (G1463A). The actual DNA sequence of the polynucleotide expression construct inserted in clone MTBO0411-1, including the mutated nucleotide in position 1463, is shown in SEQ ID NO:7. The deduced encoded variant PfuS amino acid sequence is shown in SEQ ID NO:8 including the single amino acid substitution in position 369 of the mature polypeptide: G369D, resulting from the G1463A nucleotide mutation.

The MTBO0411-1 clone was cultivated for 2 to 5 days at 37° C. For subsequent purification or enzyme protein activity measurements, the cell-free culture supernatant was heat treated at 70° C. degrees for 20 min followed by centrifugation to deactivate endogenous proteases from the expression host and removal of degenerated protein. Successful expression of PfuS protease was determined by SDS-PAGE analysis (see Example 2).

For comparison we also put together a PfuS protease expression construct which included a functional *Bacillus* secretion signal. The expression of the PfuS protease including an amino-terminal signal peptide was done as outlined above, except the following primer pair was used to PCR amplify the DNA fragment:
forward primer: tcatcgatcgcatcggctgcacctgagaagaaagttg (SEQ ID NO:9)
reverse primer: ccaaggccggtttttatgtttatggtgatgagccaggc (SEQ ID NO:10)

The resulting expression vector construct consisted of the same coding sequence as in the above fused in frame to the DNA encoding the *B. clausii* aprH protease signal peptide:
atgaaaaaaccgctggggaaaattgtcgcaagcaccgcactactcatttctgtt-gcttttagttcatcgatcgcatcggctgca cctagg (SEQ ID NO: 11), where the nucleotides in positions 1-81 encode the AprH signal and nucleotides 82-90 are left over from the cloning process).

Cloning and transformation was done as in the above and a *B. subtilis* expression clone was selected denoted MTBO0411-2, carrying the pfuS gene fragment shown in SEQ ID NO:12 encoding the deduced amino acid sequence shown in SEQ ID NO:13.

Example 2. Detection of Protease Activity and Enzyme Yield

The protease activity of the raw culture broth solution as well as the culture broth supernatant of the two selected clones from Example 1 was measured by adding 10 µL of the heat treated samples in holes that were punched in solidified Luria Bertani agar medium containing 1% of casein (solubilized skimmed milk powder). A clearing zone around the hole after incubation for 18 h at 70° C. indicated proteolytic activity.

A *B. subtilis* control host strain that is deficient of the PfuS gene did not produce a clearing zone, while the *B. subtilis* clones bearing the PfuS construct without a signal peptide from Example 1 a showed a distinct clearing zone of 10 mm radius already after 2 days of fermentation. The clearing zone of the PfuS gene construct with a signal peptide from Example 1 was not significantly different compared to the control *B. subtilis* host strain after 2 days of fermentation (about 1 mm). Only after 5 days of fermentation in shake flasks we were able to detect a significant clearing of 5 mm from the clone expressing the PfuS protease with the AprH signal peptide.

Together with results from SDS-PAGE analysis, we concluded that a much higher expression level of the PfuS protease was achieved from expression without any signal peptide than from expression with the otherwise well-known and effective signal peptide from the AprH protease which did not lead to any significant expression after 2 days of fermentation.

TABLE 1

Clearing zone radius in mm.

| Fermentation | No signal peptide | AprH signal peptide | *B. subtilis* control |
|---|---|---|---|
| 2 days at 26 C. | 8 | 1 | 0 |
| 2 days at 37 C. | 10 | 3 | 0 |
| 5 days at 26 C. | 10 | 3 | 0 |
| 5 days at 37 C. | 10 | 3 | 0 |

Successful expression of the variant PfuS protease was analysed by SDS-PAGE using cell-free fermentation culture supernatants. A distinct protein band of approximately 40 kDa indicated successful PfuS expression into the culture medium. Lysis of the *B. subtilis* cells was not actively induced during or after fermentation, which is advantageous for industrial production purposes.

SDS-PAGE analysis of all recombinantly expressed PfuS enzyme samples indicated that the expression level of the gene construct with no secretion signal in Example 1 was significantly higher than previously reported (See, e.g., EP0994191A1; Takara, JP) and also significantly higher than from the construct with a secretion signal in Example 1 above, which was similar to enzyme yields previously reported in EP0994191A1 (Takara, JP), i.e. in the range of 13-60 mg/L culture.

The recombinant purified variant PfuS protease (sample ID U43PS) showed a melting temperature of 103 deg C. by differential calorimetry in 50 mM acetate buffer, pH 5 at a scan rate of 200 K/h.

The mature amino terminal of the recombinant PfuS was determined to be AELEGLD by N-terminal aa sequencing, and the measured intact mass was 43066.4 Dalton, which was expected according to the described mature variant peptide of PfuS with the introduced point mutation: G369D shown in SEQ ID NO:8 which has a calculated mass of 43,061 Da; as opposed to the calculated mass of 43,003 Dalton of the wildtype mature PfuS polypeptide shown in SEQ ID NO:6.

The activity of Protease PfuS was also determined spectroscopically by the method employed in EP0994191A1 (Takara, JP) by measuring the amount of para-nitroaniline generated in an enzymatic hydrolysis reaction using Suc-Ala-Ala-Pro-Phe-p-NA (Sigma) as substrate. Briefly, an enzyme preparation was appropriately diluted for adequate measuring (i.e. 500 fold and 1000 fold dilutions of cell free culture supernatant with double distilled water). 50 mu L of 1 mM Suc-Ala-Ala-Pro-Phe-p-NA solution in 100 mM phosphate buffer, pH 7.0 was added to 50 mu L of the diluted sample solution. Then, the reaction was allowed to proceed at 95° C. for 30 minutes. After terminating the reaction by cooling on ice, the absorbance at 405 nm was measured to calculate the amount of para-nitroaniline generated. One unit of the enzyme was defined as the amount of the enzyme which generated 1 mu mole of p-nitroaniline per 1 minute at 95° C. The amount of enzyme protein expressed in the culture supernatant or the cells was calculated based on the measured enzymatic activity assuming the specific activity was 9.5 U/mg protein of protease PfuS as stated in US 2004 0888588. The absorption coefficient of para-NA is 8800 M-1cm-1 at 410 nm, pH 7.5 and we used the same coefficient in the reaction of this example at pH 7.0, measured at 405 nm. Using Beer-Lambert's law, the absorption value 1 in a 1 cm cuvette represents 113.6 mu M para-NA.

The calculated enzyme expression yields from the absorption values from the 500 fold and 1000 fold sample dilutions (shown in table 2) correlate very well with the estimations from the clearing zone radius measurements and the estimations by SDS-PAGE. The expression yield was in the range of 2-26 mg/L for the construct with AprH signal peptide and >5-fold higher (108 to 167 mg/L) of the construct without signal peptide.

TABLE 2

Measured absorption values (average from 3 independent experiments) and calculated enzyme expression yield after Beer-Lambert's law.

| | No signal peptide | AprH signal peptide |
|---|---|---|
| Absorption | | |
| 500x dil | 1.08 A | 0.17 A |
| 1000x dil | 0.7 A | 0.01 A |
| Enzyme Yield | | |
| 500x dil | 167 mg/L | 26 mg/L |
| 1000x dil | 108 mg/L | 2 mg/L |

Example 3. Protease Characterization

Suc-AAPF-pNA Protease Activity Assay:
pNA substrate: Suc-AAPF-pNA (Bachem L-1400).
Temperature: Room temperature (25° C.)
Assay buffer: 100 mM succinic acid, 100 mM HEPES, 100 mM CHES, 100 mM CABS, 1 mM $CaCl_2$, 150 mM KCl, 0.01% Triton X-100, pH 9.0.
20 µl protease (diluted in 0.01% Triton X-100) was mixed with 100 µl assay buffer. The assay was started by adding 100 µl pNA substrate (50 mg dissolved in 1.0 ml DMSO and further diluted 45× with 0.01% Triton X-100). The increase in $OD_{405}$ was monitored as a measure of the protease activity.

Protease Purification

The culture broth was centrifuged (20000×g, 20 min) and the supernatant was carefully decanted from the precipitate. The supernatant was filtered through a Nalgene 0.2 µm filtration unit in order to remove the rest of the *Bacillus* host cells. Solid $(NH_4)_2SO_4$ was added to the 0.2 µm filtrate to 0.85 M final concentration and the salt adjusted filtrate was applied to a Phenyl-sepharose FF (high sub) column (from GE Healthcare) equilibrated in 100 mM $H_3BO_3$, 10 mM MES, 2 mM $CaCl_2$, 0.9 M $(NH_4)_2SO_4$, pH 6.0. After washing the column with the equilibration buffer, the protease was eluted with a linear gradient between the equilibration buffer and 100 mM $H_3BO_3$, 10 mM MES, 2 mM $CaCl_2$, pH 6.0+25% (v/v) 2-propanol over five column volumes. Fractions from the column were analysed for protease activity (using the Suc-AAPF-pNA assay at pH 9) and peak-fractions were pooled. The pool from the Phenyl-sepharose FF column was transferred to 10 mM Tris/HCl, 1 mM $CaCl_2$, pH 9.0 on a G25 sephadex column (from GE Healthcare). The G25 filtrate was applied to a Q-sepharose FF column (from GE Healthcare) equilibrated in 10 mM Tris/HCl, 1 mM $CaCl_2$, pH 9.0. After washing the column with the equilibration buffer, the protease was eluted with a linear NaCl gradient (0→0.5 M) in the same buffer over five column volumes. Fractions from the column were analysed for protease activity (using the Suc-AAPF-pNA assay at pH 9) and active fractions were analysed by SDS-PAGE. Fractions, where only one band was seen on the coomassie stained SDS-PAGE gel were pooled as the purified preparation and was used for further experiments.

Determination of the N-terminal sequence by EDMAN degradation was: AELEGLD. The relative molecular weight as determined by SDS-PAGE was approx. $M_r$=41 kDa. The molecular weight determined by Intact molecular weight analysis was 43,062.4 Da. This corresponds well to the calculated molecular weight based on the mature sequence shown in SEQ ID NO:8 of 43,061.3 Da.

Example 4. Cloning and Expression of the *Dictyoglomus thermophilum* Xylanase The *Bacillus licheniformis* host strain harbour deletions in the spoIIAC, aprL, mprL, cypX, sacB, bprAB, epr, vpr, and wprA genes, respectively, encoding the sporulation transcription factor sigma F, the alkaline protease, the glu-specific protease (C-component), the cytochrome P450-like enzyme CypX, the levansucrase, the bacillopeptidase F (two genes), the two extracellular serine proteases and the cell wall-associated protease WprA. Expression of the forD gene encoding a 10 kDa background protein was also reduced or eliminated by a mutation in its ribosome binding site. In addition, the *B. licheniformis* host strain is unable to produce alpha-amylase, cellulase and beta-galactosidase due to inactivation or elimination of the encoding genes.

The *B. licheniformis* strain host has been further modified by inserting an artificial promoter, a marker gene and an attB integrase recognition site from the lactococcal phage TP901-1 in the two chromosomal loci amyL and gntP in order to serve as integration sites in phage integrase-assisted site-specific integration of an expression cassette (as disclosed in WO 2006/042548).

Two strains were constructed herein using phage integrase-assisted site-specific integration of an artificial *Dictyoglomus thermophilum* xylanase expression cassette, wherein the coding sequence had been codon-optimized for expression in *B. licheniformis*.

A codon-optimized gene (shown in SEQ ID NO:14) encoding the mature xylanase xynDt (shown in SEQ ID NO:15) was cloned into a suitable phage integrase-assisted integration vector flanked downstream by an attP site and upstream by a homology region for subsequent cross-out, thereby making the plasmid pJA4156 (see FIG. 1; SEQ ID NO:16). The vector was transformed into the host strain and the xylanase expression cassette was established in the two loci as outlined above in the resulting strain JA4182.

Figure 2:
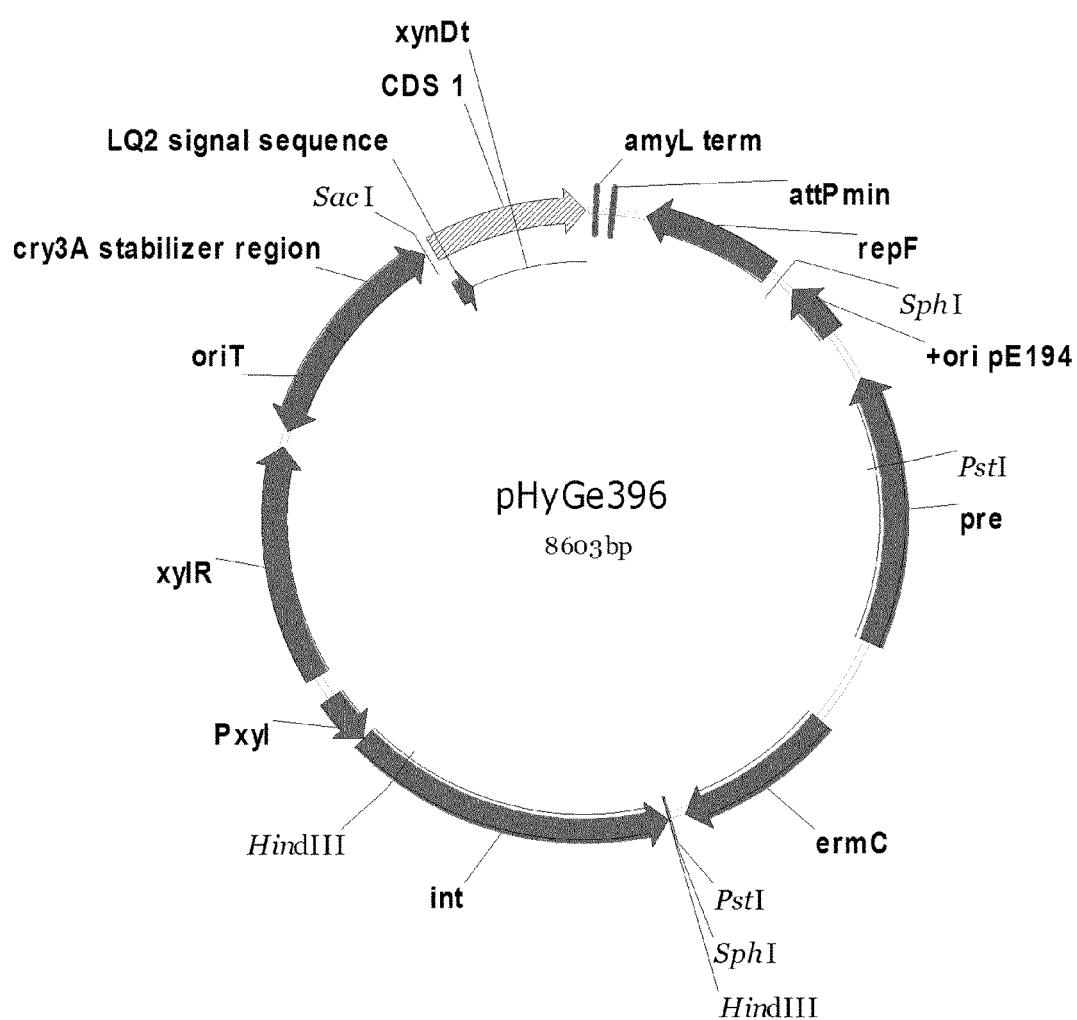
FIG. 2 shows a plasmid map of the pHyGe396 plasmid from Example 4.

The codon-optimized gene (shown in SEQ ID NO:17) encoding the mature xylanase xynDt in translational fusion with an artificial signal peptide (shown in SEQ ID NO:18) derived from the *B. licheniformis* amyL gene ($SP_{amyL}$) and known to be effective in *B. licheniformis* was cloned into a suitable phage integrase-assisted integration vector flanked downstream by an attP site and upstream by a homology region for subsequent cross-out, thereby making the plasmid pHyGe396 (see FIG. 2; SEQ ID NO:19). The vector was transformed into the host strain and the xylanase expression cassette was established in the two loci as outlined above in the resulting strain HYGE435.

The expression cassette integrated into the two integration sites in each strain encodes only the mature xylanase-part of the native two-domain *D. thermophilum* xylanase enzyme, its native C-terminal cellulose-binding domain was not included nor was its native signal peptide (or leader sequence) included. However, the xylanase expression cassette integrated into the HyGe435 strain did contain an artificial signal peptide derived from the *B. licheniformis* amyL gene ($SP_{amyL}$) and known to be effective in *B. licheniformis*, the signal peptide was in translational fusion with the mature xylanase-encoding sequence. In contrast, the xylanase expression cassette integrated into the JA4182 strain had no signal peptide-encoding sequence; the translational start-codon ATG was simply added to the 5'-end of the coding sequence of the mature xylanase.

JA4182 (amyL::xynDt; gntP::xynDt)
HYGE435 (amyL::$SP_{amyL}$_xynDt; gntP::$SP_{amyL}$_xynDt; ipsA$^-$; prsA$^+$)

Further, the HyGe435 strain has a deletion of the ispA intracellular protease-encoding gene and it carries an additional integrated prsA chaperone-encoding gene. Both the ispA deletion and the prsA gene were expected to increase the yield of the xylanase somewhat in the HyGe435 strain.

Example 5. Assay for Measurement of Activity of *D. thermophilum* Xylanase Activity The method is used to measure Xylanase activity in fermentation samples. The reaction is performed in two steps:
1) Xylanase hydrolyses wheat arabinoxylan (pH 6.0, 37° C.) to release reducing carbohydrate.
2) The reaction is stopped by the addition of an alkaline reagent containing PAHBAH and Bismuth (pH>10, 37° C.) which complexes with reduced sugars producing a colourimetric readout able to be measured at 405 nM. The colour produced is proportional to the Xylanase activity present in the sample.

Fermentation samples are weighed, dilutions prepared and the assay was performed on an analytical robot. Samples are measured on a plate reader, for example, the integrated Molecular Devices SOFTMAX PRO® plate reader.

Buffers and Reagents
Aces Buffer:

| | |
|---|---|
| ACES, N-(2-acetoamido)-2-aminoethanesulfuric acid, $C_4H_{10}N_2O_4S$ (Sigma A9758) | 9.11 g |
| 10% Triton X-100 Solution (in MQ $H_2O$) | 1000 ul |
| MQ$H_2O$ | Up to 1000 ml | pH Adjusted to 6.0 with NaOH

2×MES Buffer:

| | |
|---|---|
| MES 2-8(N-morphiline)-ethanesulfuric acid $C_5H_{13}NO_4S_1.xH_2O$ (Sigma M5287) | 19.258 g |
| MQ$H_2O$ | Up to 1000 ml | pH Adjusted to 6.0 with NaOH

PAHBAH:

| | |
|---|---|
| Bismuth (III)-acetate $(CH_3CO_2)_3Bi$ (Sigma 401587) | 0.552 g |
| PAHBAH (Sigma H9882) | 2 g |
| Potassium Sodium Tartrate, tetrahydrate, $C_4H_4KNaO_6 \cdot 4H_2O$ (Merck 1.08087) | 5 g |
| 500 mM NaOH | Up to 100 ml |

1% w/v Arabinose:

| | |
|---|---|
| Wheat flour Arabinoxylan, medium viscosity (Megazyme, P-WAXYM) | 3 g |
| 95% Ethanol | 24 ml |
| MQ$H_2O$ | Up to 300 ml |

Arabinose-MES Substrate Buffer:
Mix equal parts of 1% Arabinose with 2×MES buffer, the volume of which is according to assay requirements.

Assay Procedure
Preparation of Standard:
The standard used is a xylanase sample with a stated concentration (for the measurements below it was 4.03 mg/ml). The standard is thawed to ambient temperature prior to use. The standard is diluted to a starting dilution of 1 µg/ml.

The standard is diluted (in quadruplicate) as follows.

| ACES buffer (µl) | 1 µg/ml Diluted Standard (µl) | Standard Concentration (µg/ml) |
|---|---|---|
| 0 | 200 | 1 |
| 50 | 175 | 0.075 |
| 100 | 150 | 0.05 |
| 150 | 100 | 0.025 |
| 175 | 50 | 0.0125 |
| 200 | 0 | 0 |

All assay steps are performed on a customised BIOMEK® (Beckman Coulter) liquid handling system with an integrated balance, Span8 pippetting system and SPECTRAMAX® (Beckman Coulter) plate reader.

Sample Preparation:
1) If the Full Culture broth samples are extremely thick and viscous then the samples are initially prepared by shaking in a 24 well plate with steel ball bearings (6 mm diameter) at 900 rpm for 15 minutes. After which time they are transferred to the robot balance using a wide bore pippette and weighed to give an approximate 10 fold initial dilution in ACES buffer (the actual weight/initial dilution is subsequently corrected for in the final calculations). Typically this initial step is 200 µl of culture broth added to 1800 µl ACES buffer. If samples are received as supernatants or can comfortably be pippetted, then the initial dilution is performed as a straightforward liquid to liquid pippetting step.
2) The weighed samples are then distributed in triplicate and diluted plate wise according to their predicted activity in ACES buffer in 96 well microtitre plates. With the final 2 dilution plates falling within the standard curve according to their predicted activity.
3) A standard curve is generated on each of the final 2 dilution plates as described above.
4) For each of the final 2 dilution plates, 20 µl each of the samples and standards are transferred to 110 µl of Arabinose-MES substrate buffer and immediately mixed (900 rpm for 30 seconds, robot orbital shaker).
5) The plates are sealed and incubated for 30 minutes at 37° C. with shaking (600 rpm, IKA Schüttler MTS4) in an enclosed incubator.
6) 65 µl of PAHBAH is added to the plates, after which time they are sealed and incubated for a further 15 minutes at 37° C. with shaking (600 rpm, IKA Schüttler MTS4).
7) The plates are measured for absorbance at 405 nM on the plate reader and activity is extrapolated from the resultant accompanying standard curve.

Example 6. Fed-Batch Fermentation of *B. licheniformis* Strains JA4182 and HYGE435

Fed-batch fermentations with *B. licheniformis* strains JA4182 and HYGE435 were conducted as described below. All media were sterilized by standard methods. Unless otherwise described, tap water was used. The ingredient concentrations referred to in the below recipes are before any inoculation.

First Inoculum Medium:
SSB5 agar: 10 g/l Soy peptone; Sucrose 10 g/l; Potassiumdihydrogenphosphate 2 g/l; Di-Sodiumhydrogenphosphate, 2H2O 5 g/l; Vitamins (Thiamin-dichlorid 11.4 mg/l; Riboflavin 0.97 mg/l; Nicotinic acid 7.7 mg/l; Calcium D-pantothenate 9.5 mg/l; Pyridoxal-HCl 1.9 mg/l; D-biotin 0.37 mg/l; Folic acid 0.97 mg/l); Trace metals (MnSO4, H2O 9.8 mg/l; FeSO4, 7H2O 39.25 mg/l; CuSO4, 5H2O 3.9 mg/l; ZnCl2 3.9 mg/l); 25 g/l agar adjusted to pH 7.3-7.4 with 4N NaOH.

Transfer Buffer:
M-9 buffer (deionized water is used for the preparation): Di-Sodiumhydrogenphosphate, 2H2O 8.8 g/l; Potassiumdihydrogenphosphate 3 g/l; Sodium Chloride 4 g/l; Magnesium sulphate, 7H2O 0.2 g/l.

Inoculum Shake Flask Medium (Concentration is Before Inoculation):
PRK-50: 110 g/l soy grits; Di-Sodiumhydrogenphosphate, 2H2O5 g/l; pH adjusted to 8.0 with NaOH/H3PO4 before sterilization.

Make-Up Medium (Concentration is Before Inoculation):
Tryptone (Casein hydrolysate from Difco) 30 g/l; Magnesium sulphate, 7H2O 4 g/l; Di-Potassiumhydrogenphosphate 7 g/l; Di-Sodiumhydrogenphosphate, 2H2O 7 g/l; Di-Ammoniumsulphate 4 g/l; Citric acid 0.78 g/l; Vitamins (Thiamin-dichlorid 34.2 mg/l; Riboflavin 2.9 mg/l; Nicotinic acid 23 mg/l; Calcium D-pantothenate 28.5 mg/l; Pyridoxal-HCl 5.7 mg/l; D-biotin 1.1 mg/l; Folic acid 2.9 mg/l); Trace metals (MnSO4, H2O 39.2 mg/l; FeSO4, 7H2O 157 mg/l; CuSO4, 5H2O 15.6 mg/l; ZnCl2 15.6 mg/l); Antifoam (SB2121) 1.25 ml/l; pH adjusted to 6.0 with NaOH/H3PO4 before sterilization.

Feed Medium:
Sucrose 708 g/l;

Procedure for Inoculum Steps:
First the strain was grown on SSB5 agar slants 1 day at 37° C. The agar was then washed with M-9 buffer, and the optical density (OD) at 650 nm of the resulting cell suspension was measured. The inoculum shake flask (PRK-50) is inoculated with an inoculum of OD (650 nm)×ml cell suspension=0.1. The shake flask was incubated at 37° C. at 300 rpm for 20 hr.

The fermentation in the main fermentor (fermentation tank) was started by inoculating the main fermentor with the growing culture from the shake flask. The inoculated volume was 11% of the make-up medium (80 ml for 720 ml make-up media).

Fermentor:
Standard lab fermentors were used equipped with a temperature control system, pH control with ammonia water and phosphoric acid, dissolved oxygen electrode to measure >20% oxygen saturation through the entire fermentation.

Fermentation Parameters:
Temperature: 41° C.

The pH was kept between 6.8 and 7.2 using ammonia water and phosphoric acid.

Control: 6.8 (ammonia water); 7.2 phosphoric acid.
Aeration: 1.5 liter/min/kg broth weight.
Agitation: 1350 rpm.

Feed Strategy:
0 hr. 0.05 g/min/kg initial broth after inoculation
8 hr. 0.156 g/min/kg initial broth after inoculation
End 0.156 g/min/kg initial broth after inoculation Experimental Setup:

The fermentation was run for tree days.

Results:

The relative xylanase activity in the supernatant was determined at day 3:

| Strain | Activity | Comment |
| --- | --- | --- |
| JA4182 | 446% | No signal peptide |
| HyGe435 | 100% | Signal peptide |

Contrary to expectations, the xylanase yield was much higher from the *B. licheniformis* host strain JA4182, where the enzyme was expressed without any signal peptide whatsoever. The observed yield was more than 1000-fold higher than previously reported when expressing the full *D. thermophilum* xylanase coding sequence including its native signal in *Bacillus subtilis* which was only about 1.4 mg/l after recovery (see Table 1 of Zhang et al; Appl Biochem Biotechnol (2010) 160:1484-1495).

Preferred Embodiments

[1] An isolated synthetic polynucleotide encoding a protease polypeptide with no secretion signal, said protease polypeptide having an amino acid sequence at least 80% identical to the protease shown in positions 1 to 413 of SEQ ID NO:8.

[2] The polynucleotide according to embodiment 1, wherein the encoded protease polypeptide comprises or consists of an amino acid sequence at least 80% identical to the protease shown in positions 1 to 413 of SEQ ID NO:8.

[3] The polynucleotide according to embodiment 1 or 2, which has a nucleotide sequence at least 80% identical to the sequence shown in positions 1 to 1569 of SEQ ID NO:7; preferably at least 80% identical to the sequence shown in positions 331 to 1569 of SEQ ID NO:7.

[4] The polynucleotide according to any of embodiments 1-3, which comprises or consists of a nucleotide sequence at least 80% identical to the sequence shown in positions 1 to 1569 of SEQ ID NO:7; preferably at least 80% identical to the sequence shown in positions 331 to 1569 of SEQ ID NO:7.

[5] A nucleic acid construct or an expression vector comprising a polynucleotide as defined in any of embodiments 1 to 4 operably linked to control sequences that provide for its expression in a host cell of choice.

[6] A prokaryotic host cell transformed with or comprising a polynucleotide as defined in embodiments 1 to 4, or a nucleic acid construct or an expression vector as defined in embodiment 5, wherein said host cell is capable of producing the protease polypeptide.

[7] The host cell of embodiment 6 which is a *Bacillus* host cell.

[8] The host cell of embodiment 7, wherein the *Bacillus* host cell is selected from the group of *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis*.

[9] The host cell of any of embodiments 6 to 8, wherein the protease polypeptide comprises or consists of an amino acid sequence at least 80% identical to the protease shown in positions 1 to 413 of SEQ ID NO:8.

[10] A method of producing a protease polypeptide, the method comprising the steps of:
a) cultivating a host cell as defined in any of embodiments 6 to 9 under conditions conducive to the expression of the protease polypeptide; and, optionally,
b) recovering the protease.

[11] An isolated synthetic protease polypeptide having the amino acid sequence shown in positions 1 to 413 of SEQ ID NO:8.

[12] The polypeptide of embodiment 11 comprising or consisting of the amino acid sequence shown in positions 1 to 413 of SEQ ID NO:8.

[13] The polypeptide of embodiment 11 or 12, which is an isolated protease having at least 80% sequence identity to the protease shown in positions 1 to 413 of SEQ ID NO: 6, wherein the protease comprises a substitution at position 369.

[14] The polypeptide of embodiment 11 or 12, which is a substitution variant of the mature PfuS protease shown in positions 1 to 413 of SEQ ID NO:6, wherein the glycine in position 369 is substituted for an aspartic acid: G369D.

[15] A composition comprising a protease polypeptide as defined in any of embodiments 11 to 14.

The invention claimed is:

1. A recombinant *Bacillus* host cell comprising an expression vector encoding a natively secreted protease without a signal peptide,
   wherein the expression vector lacks a signal peptide coding sequence; and
   wherein the protease comprises or consists of an amino acid sequence at least 90% identical to the sequence shown in positions 1 to 413 of SEQ ID NO: 8.

2. The recombinant *Bacillus* host cell according to claim 1, which is a *Bacillus* host cell selected from the group consisting of *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis*.

3. The recombinant *Bacillus* host cell according to claim 1, wherein the protease comprises or consists of an amino acid sequence at least 95% identical to the sequence shown in positions 1 to 413 of SEQ ID NO: 8.

4. The recombinant *Bacillus* host cell according to claim 1, wherein the protease comprises or consists of an amino acid sequence at least 97% identical to the sequence shown in positions 1 to 413 of SEQ ID NO: 8.

5. The recombinant *Bacillus* host cell according to claim 1, wherein the protease comprises or consists of an amino acid sequence at least 98% identical to the sequence shown in positions 1 to 413 of SEQ ID NO: 8.

6. The recombinant *Bacillus* host cell according to claim 1, wherein the protease comprises or consists of an amino acid sequence at least 99% identical to the sequence shown in positions 1 to 413 of SEQ ID NO: 8.

7. The recombinant *Bacillus* host cell according to claim 1, wherein the protease comprises amino acids 1 to 413 of SEQ ID NO: 8.

8. The recombinant *Bacillus* host cell according to claim 1, wherein the protease consists of amino acids 1 to 413 of SEQ ID NO: 8.

9. The recombinant *Bacillus* host cell according to claim 1, wherein the protease is encoded by a polynucleotide comprising or consisting of a nucleotide sequence at least 90% identical to the sequence shown in positions 1 to 1569 of SEQ ID NO: 7.

10. The recombinant *Bacillus* host cell according to claim 1, wherein the protease is encoded by a polynucleotide comprising or consisting of a nucleotide sequence at least 90% identical to the sequence shown in positions 331 to 1569 of SEQ ID NO: 7.

11. A method of recombinantly producing a natively secreted polypeptide, the method comprising the steps of:
   a) providing a *Bacillus* host cell of claim 1 comprising an expression vector encoding a natively secreted protease without a signal peptide,
      wherein the expression vector lacks a signal peptide coding sequence:
      wherein the protease comprises or consists of an amino acid sequence at least 90% identical to the sequence shown in positions 1 to 413 of SEQ ID NO: 8; and
   b) cultivating the *Bacillus* host cell under conditions conducive to the expression of the protease.

12. The method according to claim 11, wherein the *Bacillus* host cell is selected from the group consisting of *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis*.

13. The method according to claim 11, wherein the protease comprises or consists of an amino acid sequence at least 95% identical to the sequence shown in positions 1 to 413 of SEQ ID NO: 8.

14. The method according to claim 11, wherein the protease comprises or consists of an amino acid sequence at least 97% identical to the sequence shown in positions 1 to 413 of SEQ ID NO: 8.

15. The method according to claim 11, wherein the protease comprises or consists of an amino acid sequence at least 98% identical to the sequence shown in positions 1 to 413 of SEQ ID NO: 8.

16. The method according to claim 11, wherein the protease comprises or consists of an amino acid sequence at least 99% identical to the sequence shown in positions 1 to 413 of SEQ ID NO: 8.

17. The method according to claim 11, wherein the protease comprises amino acids 1 to 413 of SEQ ID NO: 8.

18. The method according to claim 11, wherein the protease consists of amino acids 1 to 413 of SEQ ID NO: 8.

19. The method according to claim 11, wherein the protease is encoded by a polynucleotide comprising or consisting of a nucleotide sequence at least 90% identical to the sequence shown in positions 1 to 1569 of SEQ ID NO: 7.

20. The method according to claim 11, wherein the protease is encoded by a polynucleotide comprising or consisting of a nucleotide sequence at least 90% identical to the sequence shown in positions 331 to 1569 of SEQ ID NO: 7.

* * * * *